United States Patent [19]

Tamburini et al.

[11] Patent Number: 5,407,931
[45] Date of Patent: Apr. 18, 1995

[54] DERIVATIVES OF 1-AZATRICYCLO[7.2.03,8]UNDEC-2-ENE-2-CARBOXYCLIC ACID

[75] Inventors: Bruno Tamburini, San Pietro in Cariano; Alcide Perboni, San Giorgio di Mantova; Tino Rossi, Verona; Daniele Donati, Soave; Daniele Andreotti, Tresigallo; Giovanni Gaviraghi; Roberto Carlesso, both of Verona; Claudio Bismara, Oppeano, all of Italy

[73] Assignee: Glaxo S.p.A., Verona, Italy

[21] Appl. No.: 578,948

[22] Filed: Sep. 7, 1990

[30] Foreign Application Priority Data

Sep. 8, 1989 [GB] United Kingdom ............. 8920337
Jul. 13, 1990 [GB] United Kingdom ............. 9015484

[51] Int. Cl.$^6$ .................. C07D 487/00; A01N 43/00; A61K 31/395
[52] U.S. Cl. ..................................... 514/210; 540/350
[58] Field of Search ........................ 540/302; 514/210

[56] References Cited

U.S. PATENT DOCUMENTS 4,374,848 2/1983 Christensen et al. ............. 514/210
4,374,849 2/1983 Christensen et al. ............. 514/210
4,600,713 7/1986 Christensen et al. ............. 514/210

OTHER PUBLICATIONS

Reider et al., Tetrahedron Letters, 23, 4, 379–382, 1982.
Tetrahedron Letter vol. 22, No. 50, 5027–5030 1981, by J. V. Heck et al.

Primary Examiner—Johann Richter
Assistant Examiner—Rebecca Cook
Attorney, Agent, or Firm—Bacon & Thomas

[57] ABSTRACT

The invention relates to heterocyclic derivatives having antibacterial activity, to processes for their preparation, to compositions containing them, and to their medicinal uses. The derivatives according to the invention have the following general formula:

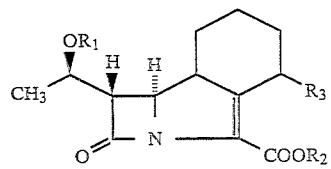

23 Claims, No Drawings

DERIVATIVES OF 1-AZATRICYCLO[7.2.03,8]UNDEC-2-ENE-2-CARBOXYLIC ACID

This invention relates to heterocyclic derivatives having antibacterial activity, to processes for their preparation, to compositions containing them, and to their use in medicine.

Thus the present invention provides compounds of the general formula (I)

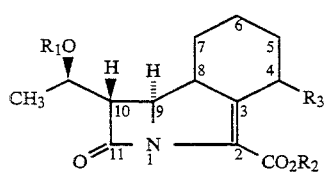

in which $R_1$ represents a hydrogen atom or a hydroxyl protecting group;

$R_2$ represents a hydrogen atom, a carboxyl protecting group or a cation derived from an inorganic base or an organic base;

$R_3$ represents a hydrogen atom, a hydroxyl, hydroxylmethyl or $C_{1-3}$alkyl group, or a group $XR_4$ in which X represents an oxygen atom or the group $S(O)n$ in which n is zero or the integer 1 or 2 and $R_4$ represents a $C_{1-5}$alkyl, $C_{3-7}$cycloalkyl, or phenyl group, or when X is an oxygen or sulphur atom then $R_4$ may also represent the group $AlkNR_5R_6$ in which Alk represents a $C_{2-6}$ straight or branched alkylene chain, and $R_5$ and $R_6$ each independently represent a hydrogen atom or a $C_{1-4}$ alkyl group or $R_5$ represents a formyl, acetyl or iminomethyl group and $R_6$ represents a hydrogen atom or $R_5$ and $R_6$ together with the nitrogen atom to which they are attached form a pyrrolidino or piperidino ring, or the group $R_3$ represents the group $(CH_2)_mNR_7R_8$ in which m is zero or one and $R_7$ and $R_8$ independently each represent a hydrogen atom or a $C_{1-4}$alkyl group or $R_7$ represents a formyl, acetyl or iminomethyl group and $R_8$ represents a hydrogen atom or the group $R_3$ and the carbon atom to which it is attached represents a keto group or a ketal derivative thereof; and metabolically labile esters, salts and solvates thereof.

When the group $R_3$ contains a basic centre acid addition salts of such compounds and internal salts formed with the carboxylic acid grouping ($R_2$=H) are also included in the invention.

In addition to the fixed stereochemical arrangement as defined in formula (I) the molecule contains a further asymmetric carbon atom at the 8-position, and another at the 4-position, when $R_3$ is other than a hydrogen atom or when $R_3$ and the carbon atom to which it is attached forms a keto group or a ketal derivative thereof. It will be appreciated that all stereoisomers including mixtures thereof arising from these additional asymmetric centres, are within the scope of the compounds of formula (I).

The compounds of formula (I) are antibacterial agents and/or of use as intermediates for the preparation of other active compounds within the general formula (I). Compounds wherein $R_1$ represents a hydroxyl protecting group and/or wherein $R_2$ represents a carboxyl protecting group are in general intermediates for the preparation of other compounds of formula (I).

Suitable hydroxyl protecting groups $R_1$ and carboxyl protecting groups $R_2$ include those which may be removed by hydrolysis under buffered conditions or under non-aqueous conditions.

When the group $OR_1$ is a protected hydroxyl group this is conveniently an ether or an acyloxy group. Examples of particularly suitable ethers include those in which $R_1$ is a hydrocarbylsilyl group such as trialkylsilyl, e.g. trimethylsilyl or t-butyldimethylsilyl. When the group $OR_1$ represents an acyloxy group then examples of suitable groups $R_1$ includes alkanoyl e.g. acetyl, pivaloyl; alkenoyl e.g. allylcarbonyl; aroyl e.g. p-nitrobenzoyl; alkoxycarbonyl e.g. t-butoxcarbonyl; haloalkoxycarbonyl e.g. 2,2,2-trichloroethoxycarbonyl, or 1,1,1-trichloro-2-methyl-2-propoxycarbonyl; aralkyloxycarbonyl e.g. benzyloxycarbonyl or P-nitrobenzyloxycarbonyl; or alkenyloxycarbonyl e.g. allyloxycarbonyl.

A particularly convenient protecting group $R_1$ is t-butyldimethylsilyl.

Examples of suitable carboxyl protecting groups include arylmethyl groups such as benzyl, p-nitrobenzyl or trityl, or alkenyl groups such as allyl or substituted allyl, t-butyl, haloalkyl e.g. trichloroethyl or trialkylsilylalkyl e.g. trimethylsilylethyl. Preferred protecting groups $R_2$ include arylmethyl e.g. benzyl or allyl.

When the group $R_3$ together with the carbon atom to which it is attached represents a ketal group then the ketal is conveniently that derived from a $C_{1-3}$ alkanol e.g. methanol or a 1,2 or 1,3 alkane diol such as glycol or propane 1,3-diol.

Particularly useful compounds of formula (I) for use in medicine as antibacterial agents are those in which the group $R_1$ represents a hydrogen atom and $R_2$ represents a hydrogen atom or a physiologically acceptable cation, or an internal salt thereof. These compounds exhibit antibacterial activity against a wide range of gram positive and gram negative, aerobic and anaerobic pathogenic microorganisms.

Where $R_2$ is a physiologically acceptable cation, suitable cations include those of alkali metals (e.g. sodium or potassium), alkaline earth metals (e.g. calcium), amino acids (e.g. lysine and arginine) and organic bases (e.g. procaine, phenylbenzylamine, dibenzylethylenediamine, ethanolamine, diethanolamine, and N-methyl glucosamine).

Where $R_2$ is a cation that is not physiologically acceptable then such compounds may be useful as intermediates for the preparation and/or isolation of other compounds of the invention.

Metabolically labile esters of the compounds of formula (I) include alkyl esters for example $C_{1-4}$alkyl esters such as methyl ethyl or isopropyl esters or alkenyl esters such as allyl or substituted allyl esters.

The general formula (I) as drawn includes at least 4 stereoisomers and mixtures thereof and these may be represented by the formulae (1a, 1b, 1c and 1d).

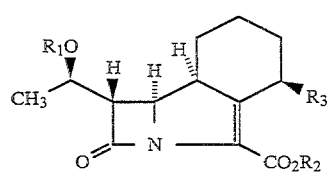

-continued

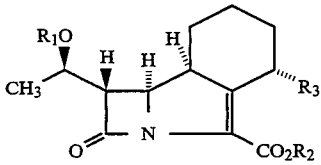
Ib

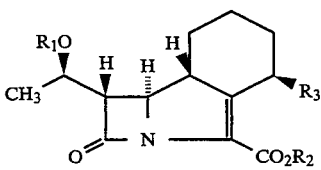
Ic

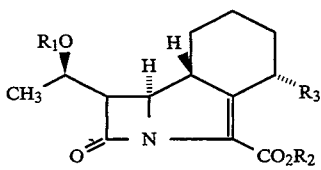
Id

The wedge shaped bond ◂ indicates that the bond is above the plane of the paper. The broken bond indicates that the bond is below the plane of the paper.

The configuration shown for the carbon atom at the 8-position in formulae 1a and 1b is hereinafter referred to as the β configuration and in formulae 1c and 1d as the α configuration.

The configuration shown for the carbon at the 4 position in formulae 1b and 1d is hereinafter referred to as the α configuration and in formulae 1a and 1c as the β configuration.

In general, in the specific compounds named below, the β-configuration at the 8-position corresponds to the S isomer and the β-configuration at the 4-position to the R isomer. The α configuration at the 8-position corresponds to the R isomer and the α-configuration at the 4-position corresponds to the S isomer. The assignment of the R or S configuration at the 4- and 8- positions have been made according to the rules of Cahn. Ingold and Prelog, Experientia 1956, 12, 81.

A preferred group of compounds of formula I are those in which the carbon atom at the 8- position is in the β configuration. Within this group those compounds in which the carbon atom at the 4-position is in the α configuration are particularly preferred.

A further preferred group of compounds of the invention are those in which the group $R_3$ represents a hydrogen atom or more particularly an amino, aminomethyl, methylamino, hydroxy, hydroxylmethyl, methyl, cyclopentyloxy, ethoxy, isopropoxy, methoxy, aminoethoxy, phenylthio, methylthio or methylsulphinyl group or together with the carbon atom to which it is attached form a keto group or its dimethylketal.

A particularly preferred group of compounds of formula (I) are those in which the carbon atom at the 8-position is in the β configuration and and the carbon atom at the 4-position in the α configuration, $R_1$ represents a hydrogen atom, $R_2$ represents a hydrogen atom or a physiologically acceptable cation and $R_3$ represents an amino, methylamino, aminomethyl, ethoxy, methoxy, isopropoxy, aminoethoxy, phenylthio, methylthio, methylsulphinyl, hydroxy or hydroxymethyl group, and metabolically labile esters, salts and solvates thereof.

Specific preferred compounds include (4S,8S,9R,10S,12R)-4-methoxy-10-(1-hydroxyethyl)-11-oxo-1-azatricyclo [7.2.0.0$^{3,8}$] undec-2-ene-2-carboxylic acid and salts thereof e.g. sodium or potassium salt.

(4S,8S,9R,10S,12R)-4-methylthio-10-(1-hydroxyethyl)-11-oxo-1-azatricyclo[7.2.0.0$^{3,8}$]undec-2-ene-2-carboxylic acid and salts thereof e.g. potassium or sodium salt.

(4S,8S,9R,10S,12R)-4-methylsulphinyl-10-(1-hydroxyethyl)-11-oxo-1-azatricyclo[7.2.0.0$^{3,8}$]undec-2-ene-2-carboxylic acid and salts thereof e.g. potassium or sodium salt.

(4S,8S,9R,10S,12R)-4-amino-10-(1-hydroxyethyl)-11-oxo-1-azatricyclo[7.2.0.0$^{3,8}$]undec-2-ene-2-carboxylic acid and salts thereof.

Compounds according to the invention not only exhibit a broad spectrum of antibacterial activity against a wide range of pathogenic microorganisms but also have a very high resistance to all β-lactamases. Compounds of the invention are also relatively stable to renal dehydropeptidase.

Compounds of the invention have been found to exhibit useful levels of activity against strains of *Staphylococcus aureus*, *Streptococcus faecalis*, *Escherichia coli*, *Pseudomonas aeruginosa*, *Clostridium perfringens* and *Bacteriodes fragilis*.

The compounds of the invention may therefore be used for treating a variety of diseases caused by pathogenic bacteria in human beings and animals.

Thus, according to another aspect of the present invention, we provide a compound of formula (I) for use in the therapy or prophylaxis of systemic or topical bacterial infections in a human or animal subject.

According to a further aspect of the invention we provide the use of a compound of formula (I) for the manufacture of a therapeutic agent for the treatment of systemic or topical bacterial infections in a human or animal body.

According to a yet further aspect of the invention we provide a method of treatment of the human or non-human animal body to combat bacterial infections which method comprises administering to the body an effective amount of a compound of formula (I).

The compounds of the invention may be formulated for administration in any convenient way for use in human or veterinary medicine and the invention therefore includes within its scope pharmaceutical compositions comprising a compound of the invention adapted for use in human or veterinary medicine. Such compositions may be presented for use in conventional manner with the aid of one or more suitable carriers or excipients. The compositions of the invention include those in a form especially formulated for parenteral, oral, buccal, rectal, topical, implant, ophthalmic, nasal or genito-urinary use.

The compounds according to the invention may be formulated for use in human or veterinary medicine by injection (e.g. by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

The compounds according to the invention may be formulated for topical administration, for use in human and veterinary medicine, in the form of ointments, creams, gels, lotions, shampoos, powders, (including spray powders), pessaries, tampons, sprays, dips, aerosols, drops (e.g. eye ear or nose drops) or pour-ons.

Aerosol sprays are conveniently delivered from pressurised packs, with the use of a suitable propellant, eg dichlorodifluoromethane, trichlorofluoromethane, dichlorotetrafluoroethane, carbon dioxide or other suitable gas.

For topical administration by inhalation the compounds according to the invention may be delivered for use in human or veterinary medicine via a nebuliser.

The pharmaceutical compositions for topical administration may also contain other active ingredients such as corticosteroids or antifungals as appropriate.

The compositions may contain from 0.01-99% of the active material. For topical administration, for example, the composition will generally contain from 0.01-10%, more preferably 0.01-1% of the active material.

For systemic administration the daily dose as employed for adult human treatment will range from 5-100 mg/kg body weight, preferably 10-60 mg/kg body weight, which may be administered in 1 to 4 daily doses, for example, depending on the route of administration and the condition of the patient. When the composition comprises dosage units, each unit will preferably contain 200 mg to 1 g of active ingredient.

The duration of treatment will be dictated by the rate of response rather than by arbitrary numbers of days.

The compounds of formula (I) may be prepared by the cyclisation of a compound of formula (II)

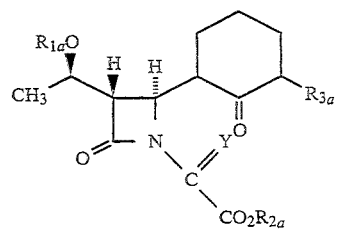

(II)

in which the group $R_{3a}$ has the meansings defined above for $R_3$ or is a group convertible thereto, and Y is an oxygen atom or a phosphine group, and the groups $R_{1a}$ and $R_{2a}$ are hydroxy and carboxyl protecting groups as defined for $R_1$ and $R_2$ and if required or desired subjecting the resulting compound prior to or subsequent to any separation into its stereochemical isomers, to one or more of the following operations (a) removal of one or more protecting groups.
(b) conversion of the group $R_{3a}$ into the group $R_3$.
(c) conversion of a compound in which $R_2$ is a hydrogen atom or a carboxyl protecting group into a salt of an inorganic or organic base.

The cyclisation of a compound of formula (II) in which Y is oxygen is conveniently carried out by heating in the presence of an organic phosphite. The reaction is preferably carried out in a solvent or mixture of solvents at a temperature within the range 60°–200°. Suitable solvents include hydrocarbons with an appropriate boiling point, for example aromatic hydrocarbons, such as toluene or xylene.

Suitable organic phosphites include acyclic and cyclic trialkylphosphites, triarylphosphites and mixed alkylarylphosphites. Particularly useful organic phosphites are the trialkylphosphites e.g. triethylphosphite or trimethylphosphite.

The cyclisation of a compound of formula (II) in which Y is a phosphine grouping is preferably carried out in a solvent at a temperature between 40°–200° C. Suitable solvents include hydrocarbons such as aromatic hydrocarbons, for example xylene or toluene, aliphatic hydrocarbons and halogenated hydrocarbons such as dichloromethane, chloroform and trichloroethane. Examples of suitable phosphine groups are triarylphosphines e.g. triphenyl phosphine, or trialkylphosphines e.g. tri-t-butylphosphine.

The hydroxyl and carboxyl protecting groups $R_{1a}$ and $R_{2a}$ may be removed by conventional procedures and in any order. More preferably however the hydroxyl protecting group $R_{1a}$ is removed prior to the removal of the carboxyl protecting group. Such removal of the protecting groups is a further feature of the invention.

The hydroxyl protecting groups may be removed by well known standard procedures such as those described in Protective Groups in Organic Chemistry, pages 46-119, Edited by J F W McOmie (Plenum Press, 1973). For example when $R_{1a}$ is a t-butyldimethylsilyl group, this may be removed by treatment with tetrabutylammonium fluoride and acetic acid. This process is conveniently carried out in a solvent such as tetrahydrofuran. Similarly when $R_{1a}$ is a trichloroethoxycarbonyl group this may be removed by treatment with zinc and acetic acid.

The carboxyl protecting group $R_{2a}$ may also be removed by standard processes such as those described in Protective Groups in Organic Chemistry, pages 192–210, Edited by J F W McOmie (Plenum Press 1973). For example when $R_{2a}$ represents an arylmethyl group this may be removed by conventional procedures using hydrogen and a metal catalyst e.g. palladium. When the group $R_{2a}$ represents an allyl or substituted allyl group then this is preferably removed by treatment with an allyl acceptor in the presence of tetrakis(triphenylphosphine) palladium and optionally in the presence of triphenylphosphine. Suitable allyl acceptors include sterically hindered amines such as tertbutylamine, cyclic secondary amines such as morpholine or thiomorpholine, tertiary amines such as triethylamine, aliphatic or cycloaliphatic β-dicarbonyl compounds such as acetylacetone, ethyl acetoacetate or dimedone, or alkanoic acids or alkali metal salts thereof such as acetic acid, propionic acid or 2-ethyl hexanoic acid or the potassium or sodium salt thereof.

A particularly useful allyl acceptor is 2-ethylhexanoic acid and more especially the sodium or potassium salts thereof.

The reaction is preferably carried out in an inert solvent such as an ether e.g. diethyl ether or tetrahydrofuran, an alkanol e.g. ethanol, an ester e.g. ethyl acetate or a halohydrocarbon e.g. methylene chloride, or mixtures thereof. The reaction is conveniently carried out in the temperature range 0°–40° more particularly at room temperature.

Compounds of the invention in which the group $R_2$ is a physiologically acceptable cation may be prepared from compounds of the invention in which $R_2$ is hydrogen by treatment with a suitable base. Conveniently the salt is formed in solution and then if required precipitated by the addition of a non-solvent e.g. a non polar aprotic solvent. Alternatively the sodium or potassium salt may be prepared by treating a solution of a compound of formula (I) in which $R_2$ represents a hydrogen atom with a solution of sodium or potassium 2-ethylhexanoate in a non-polar solvent such as diethyl ether.

For the preparation of compounds of formula I in which $R_3$ represents a hydroxyl or hydroxymethyl group the cyclisation reaction is conveniently carried out using an intermediate of formula (II) in which $R_{3a}$ is a protected hydroxyl or protected hydroxymethyl group. Suitable protected hydroxyl groups include trihydrocarbyl silyl ethers such as the trimethylsilyl or t-butyldimethylsilyl ether. The hydroxyl protecting group may then be removed at any subsequent stage in the synthesis, for example at the same time as the removal of the hydroxyl protecting group $R_{1a}$.

For the preparation of compounds of formula (I) in which $R_3$ represents a primary or secondary amino grouping or is a substituent containing such an amino grouping, the cyclisation is conveniently carried out with an intermediate of formula (II) in which the amino group present in $R_{3a}$ is in protected form, e.g. such as an allyloxycarbonylamino group. The amino protecting group may then be removed by conventional procedures. Thus for example if $R_{3a}$ is the allyloxycarbonylamino, allyloxycarbonylaminoethoxy or allyloxycarbonylaminomethyl group these may be converted into the amino, aminoethoxy or aminomethyl group using the conditions described above for converting an allyl ester into the corresponding carboxylic acid.

Compounds of formula (I) may be converted into other compounds of formula (I). Thus compounds of formula (I) wherein the group $R_2$ is a carboxyl protecting group and $R_3$ represents the group $SOR_4$ may be prepared by oxidation of the corresponding compound of formula (I) wherein $R_3$ represents the group $SR_4$. The oxidation is preferably carried out using a peracid e.g. a peroxybenzoic acid such as m-chloroperoxybenzoic acid in an organic solvent such as a halogenated hydrocarbon e.g. methylene chloride. Preferably the reaction is carried out at a low temperature e.g. −78° C. to −20° C.

Compounds of formula (I) wherein the group $R_3$ and the carbon atom to which it is attached represents a keto group and the groups $R_1$ and $R_2$ represent protecting groups may be prepared by hydrolysis of the corresponding ketal of formula (I). For example a compound of formula (I) wherein $R_3$ and the carbon atom to which it is attached represents a dimethyl ketal may be converted into the corresponding ketone by treatment with silica in the presence of an aqueous acid such as aqueous oxalic acid or aqueous sulphuric acid. The reaction is conveniently carried out in the presence of a solvent such as a halohydrocarbon e.g. methylene chloride.

Compounds of formula (I) wherein the group $R_3$ represents an hydroxyl group may be prepared by the reduction of compounds of formula (I) wherein the group $R_3$ and the carbon atom to which it is attached represent a keto group. The reduction may be carried out using a borohydride reducing agent, such as sodium borohydride, sodium cyanoborohydride, or a trialkylborohydride such as lithium trisamyl borohydride or lithium tri-sec-butylborohydride. The reaction is carried out in a solvent such as an alkanol e.g. methanol or an ether e.g. tetrahydrofuran or an aromatic hydrocarbon e.g. toluene. Thus for example the reduction may be carried out using sodium borohydride in aqueous methanol and preferably the pH of the reaction medium is maintained between 4 and 7 by the addition of a suitable acid e.g. hydrochloric acid.

Compounds of formula (I) in which $R_1$ is a hydroxyl protecting group, $R_2$ is a carboxyl protecting group and $R_3$ is an alkoxy group e.g. methoxy may be prepared by 0-alkylation of the corresponding compound of formula (I) in which $R_3$ is a hydroxyl group. The reaction may be carried out using an appropriate alkyltrifluoromethanesulphonate in the presence of a suitable base such as potassium bis (trimethylsilyl)amide.

Compounds of formula (II) in which Y=O may be prepared by treating a compound of formula (III) in which the group $R_{1a}$ and $R_{3a}$ have the meanings given above with an activated derivative of the acid (IV) in which $R_{2a}$ has the meanings defined above.

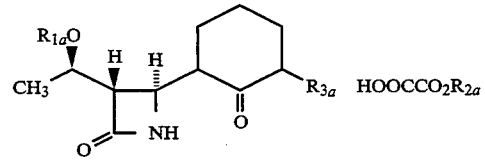

Suitable activated derivatives of the acid (IV) includes the corresponding acid halides e.g. acid chloride.

When the acid halide is used as the activated derivative of the acid (IV) then the reaction is preferably carried out in the presence of an acid acceptor such as a tertiary organic base for example pyridine or a trialkylamine in an aprotic solvent such as dichloromethane.

The compound of formula (II) in which Y is a phosphine group may be prepared by treating the intermediate (V) in which L is a leaving group such as a halogen e.g. chlorine

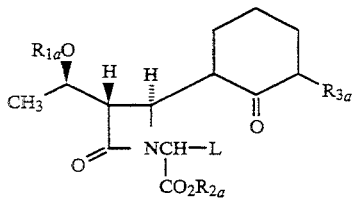 (V)

with the corresponding phosphine e.g. triphenylphosphine in the presence of a base. The reaction is conveniently carried out in a solvent such as dioxan in the presence of a tertiary organic base, e.g. 2,6 lutidine. The compounds of formula (II) are novel compounds and as such form a further aspect of the invention.

The compounds of formula (V) may be prepared from the corresponding hydroxy derivative (VI) by conventional means for converting hydroxyl groups into leaving groups.

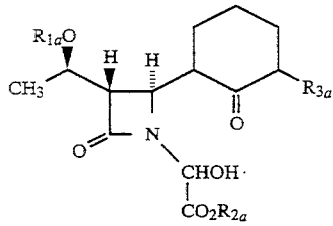 (VI)

Thus for example a compound of formula (V) in which L is a chlorine atom may be prepared by treating a compound of formula (VI) with thionyl chloride in an aprotic solvent such as dioxan or tetrahydrofuran and in the presence of a tertiary organic base e.g. 2,6-lutidine. Compounds of formula (VI) may be prepared from the reaction of a compound of formula (III) with glyoxylic ester (VII; CHOCO$_2$R$_{2a}$) preferably in the form of its hydrate or hemiacetal. The reaction is preferably carried out in an aprotic solvent such as toluene and in the presence of an activated molecular sieve. Compounds of formula (VI) may also be prepared by reduction of a compounds of formula (II) in which Y=O. Suitable reducing agents include zinc/acetic acid.

Alternatively compounds of formula (II) in which Y=O, may be prepared by oxidation of a compound of formula (VI), using for example manganese dioxide.

Compounds of formula (III) may be prepared by treating the azetidinone (VIII) with the enolate ion of the ketone (IX).

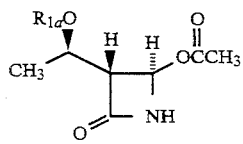 (VIII)

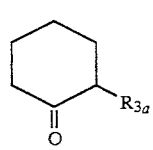 (IX)

The reaction is preferably carried out at a low temperature e.g. −78° C. in a solvent such as tetrahydrofuran.

The enolate ion of the ketone (IX) is conveniently generated in situ by treatment with a suitable base such as lithium bis(trimethyl silyl)amide.

Alternatively compounds formula (III) in which R$_{3a}$ is a hydrogen atom may be prepared from the reaction of azetidinone (VIII) with the enol ether (X)

 (X)

OSiR$_9$
R$_9$ = C$_{1-4}$alkyl

The reaction may be carried out in a solvent such as methylene chloride or acetonitrile in the presence of an activated ester of trifluoromethanesulphonic acid e.g. the trimethylsilyl ester or a Lewis acid such as stannic chloride. Compounds of formula (III) may also be prepared by reduction of a compound of formula (XI)

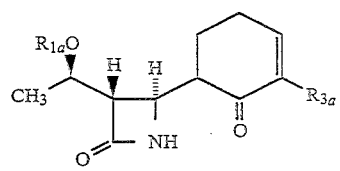 (XI)

The reduction may be effected using hydrogen and a metal catalyst e.g. palladium on a suitable support e.g. carbon or alumina. The reaction is carried out in a solvent such as an ester e.g. ethyl acetate.

The compound of formula (XI) may be prepared from the reaction of the azetidinone (VIII) with the ketone (XII) or the enol ether (XIII) using the conditions described above for preparing compounds of formula (III) from the ketone (IX) and the enol ether (X).

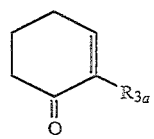 (XII)

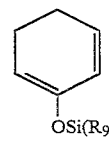 (XIII)

Compounds of formula (III) may also be prepared by oxidation of the alcohol of formula (XIV)

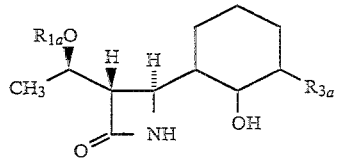 (XIV)

in which the groups $R_{1a}$ and $R_{3a}$ have the meanings defined above. The oxidation may be carried out using conventional oxidising agents known in the art for converting a secondary alcohol such as a cyclohexanol into a ketone such as a cyclohexanone. Thus for example the oxidation may be carried out using pyridinium chlorochromate or oxalyl chloride and dimethylsulphoxide. The reactions are preferably carried out in a solvent such as methylene chloride.

The alcohol (XIV) may be prepared by reduction of the $\alpha$-$\beta$ unsaturated ketone (XI). This reduction is conveniently carried out in a two stage reaction. The first stage is the reduction of the ketone to the alcohol using a suitable metal hydride such as sodium borohydride. The resultant $\alpha$-$\beta$ unsaturated alcohol is then reduced to the required alcohol (XIV) using hydrogen and a metal catalyst as described above for the preparation of the ketone (III) from the $\alpha$-$\beta$ unsaturated ketone (XI).

Compounds of formula (III) in which $R_{3a}$ represents an alkyl thio group may be prepared by treating the corresponding compound of formula (III) in which $R_{3a}$ represents a hydrogen atom with an alkali metal base e.g. lithium bis(trimethylsilyl)amide and the corresponding alkylthio methanesulphonate.

In this reaction an alkylthio group is introduced on to the N-nitrogen atom of the azetidinone group and thus it is necessary to use two equivalents of the base lithium bis(trimethylsilyl)amide and the corresponding alkylthio methanesulphonate. If the reaction is carried out stepwise, such that the alkylthio group is introduced on the azetidinone nitrogen before the second equivalent of base and alkylthio reagent is added, then the reaction gives predominantly one stereoisomer at the 4-position. If however the 2 equivalents of base and alkylthio ester are added together then the reaction gives an approximately even mixture of the two stereoisomers at the 4-position. The alkylthio group on the azetidinone nitrogen atom may be removed by treatment with a suitable nucleophile e.g. 2-mercaptopyridine in the presence of an additional tertiary organic base such as triethylamine, to give the required compound of formula (III) in which $R_3$ represents an alkylthio group.

In a modification of this process the compound of formula (III) in which $R_{3a}$ represents hydrogen may be first converted into an alternative N-protected derivative e.g. the N-trimethylsilyl derivative by conventional means and then the alkylthio group $R_{3a}$ introduced using the conditions described above followed by subsequent removal of the N-protecting group.

Compounds of formula (III) in which the group $R_{3a}$ has the meaning $SR_4$ may also be prepared from a corresponding compound in which $R_{3a}$ represents hydrogen, via a corresponding halo derivative. Thus for example reaction of a compound of formula (III) in which $R_{3a}$ is hydrogen with a suitable base such as sodium or lithium bis(trimethylsilyl) amide in a solvent such as hexane and/or tetrahydrofuran followed by reaction with iodine and then sodium sulphite gives the corresponding iodo derivative (III; $R_{3a}$=I). Treatment of the iodide with the thiol $R_4SH$ in aqueous methylene chloride in the presence of a suitable base such as a phase transfer catalyst e.g. tetrabutylammonium hydroxide gives the required compound (III: $R_{3a}$—$SR_4$).

The alcohol of formula (XIV) in which $R_{3a}$ is an alkoxy group may be prepared by reacting the corresponding epoxide (XV) with the corresponding alcohol $R_{3a}OH$ in the presence of an acid catalyst such as p-toluene sulphonic acid.

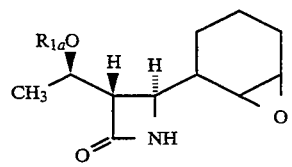

(XV)

The alcohol of formula (XIV) in which $R_{3a}$ is an azido group may be prepared by treating the expoxide (XV) with an alkali metal azide. The reaction may be carried out in a solvent such as an alkanol e.g. methanol.

The compounds of formula (III) in which the group $R_{3a}$ is an amino group may be prepared by reducing a compound of formula (III) in which the group $R_3$ is azido. The reduction may be carried out using hydrogen and a metal catalyst in a solvent such as ethyl acetate.

Compounds of formula (III) in which $R_{3a}$ is or contains a protected amino group may be prepared from the corresponding primary amino compound by conventional means for example by reaction with a suitable acid chloride such as allyloxycarbonyl chloride.

The alcohol of formula (XIV) in which $R_{3a}$ is the group $NR^7R^8$ wherein $R_7$ is a hydrogen atom or a $C_{1-4}$alkyl group and $R_8$ represents a $C_{1-4}$alkyl group may be prepared by from the reaction of the epoxide (XV) with the corresponding amine $R_7R_8NH$. The reaction is preferably carried out in a solvent such as an alkanol e.g. ethanol or aqueous ethanol and in the presence of an ammonium salt.

The alcohol of formula (XIV) in which $R_{3a}$ is a protected secondary amino group may be prepared from the corresponding secondary amino group —$NHR_8$ by conventional means, such as for example reaction with a suitable acid chloride e.g. allyloxycarbonylchloride.

The epoxide of formula (XV) may be prepared by epoxidation of the cycloalkene of formula (XVI)

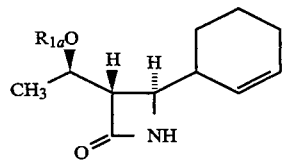

(XVI)

in which $R_{1a}$ has the meanings given above. The epoxidation may conveniently be carried out by treating the cycloalkene of formula (II) with a peracid. Suitable peracid include optionally substituted perbenzoic acids such as perbenzoic acid or meta chloroperbenzoic acid, and peralkanoic acids such as peracetic acid and trifluoroperacetic acid. The reaction may be carried out in a solvent such as a halohydrocarbon e.g. dichloromethane and conveniently at a temperature within the range $-30°$ to $+30°$ C.

The cycloalkene of formula (XVI) may be prepared by treating the corresponding tosylhydrazone (XVII)

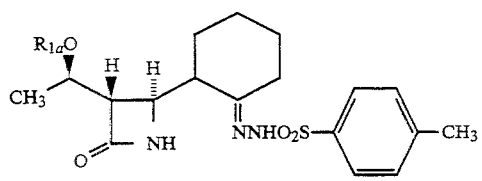

(XVII)

in which R[1] is a hydroxyl protecting group with a base, such as methyl or butyl lithium or lithium diisopropylamide. The reaction is conveniently carried out in an aprotic solvent such as an ether e.g. tetrahydrofuran and at a temperature between −50° C. to 0° C.

The tosylhydrazone (XVII) may be prepared by treating the cyclohexanone derivative (III) in which $R_{1a}$ is a hydroxyl protecting group and $R_{3a}$ is hydrogen

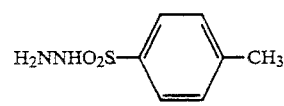

(XVIII)

with tosylhydrazide (XVIII) in a suitable solvent such as glacial acetic acid.

Compounds of formula (III) in which $R_{3a}$ is an hydroxyl group may be prepared from the silylenol ether (XIX) by reaction with a peracid such as metachloroperbenzoic acid followed by hydrolysis of the silylenol ether and the N-silyl protecting group.

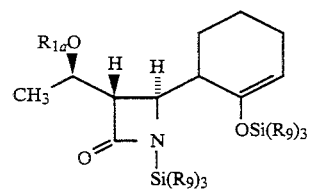

(XIX)

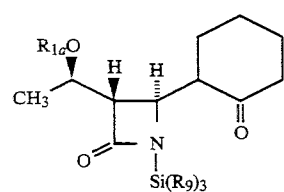

(XX)

The silylenolether (XIX) may be prepared from the corresponding ketone (XX) by reaction with a halo trialkylsilane in the presence of a strong base such as potassium or lithium bis (trimethylsilyl) amide.

The ketone (XX) may be prepared from the reaction of the N-protected azetidinone (XXI) with the enol ether (X) in the presence of an activated ester of trifluoromethyl sulphonic acid e.g. the trimethylsilyl ester or a Lewis acid such as stannic chloride.

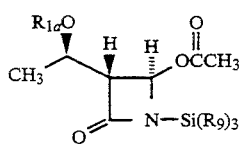

(XXI)

The N-protected azetidinone (XXI) may be prepared from the azetidinone (VIII) by reaction with an appropriate trihydrocarbylsilylhalide in the presence of a tertiary organic base such as triethylamine and in an aprotic solvent e.g. dichloromethane.

In any of the formulae (I) to (XX) shown above when there is an asymmetric carbon atom and no specific configuration is shown then the formula includes all possible configurations.

Specific stereoisomers of the compounds of formula (I) as defined in formulae 1a, 1b, 1c and 1d, essentially free of the other stereoisomers may be prepared by using the general processes described above starting with the appropriate stereoisomer of formula (III).

The processes described above for preparing the compounds of formula (III) will in general give a mixture of stereoisomers.

The individual stereoisomers of the compounds of formula (III) may be separated from each other by conventional techniques such as fractional crystallisation or more particularly by column chromatography, using for example a silica column, as illustrated in the relevant examples.

The compounds of formulae (III), (XI) and (XIV) are novel compounds and these compounds and the individual stereoisomers thereof form a further aspect of the invention.

Alternatively the synthesis may be carried out starting with a mixture of 2 or more stereoisomers of formula (III) and the required specific stereoisomer separated at by conventional techniques at another stage in the synthesis. Thus the compounds may be separated by fractional crystallisation and or column chromatography.

In the synthesis of compounds of formula (I) or the intermediates therefore it may be necessary to protect functional groupings within the group $R_3$. Such protection and deprotection steps are conventional and are within the scope of the invention. For example when the group is a primary or secondary amine or contains such a group then it may be desirable to protect these during the synthesis using conventional nitrogen protecting groups.

The compounds of formulae (VIII), (IX), (X), (XII) and (XIII) are either known compounds or may be prepared by analogous methods to those used for known compounds.

In order that the invention may be more fully understood the following examples are given by way of illustration only.

In the Preparations and Examples, unless otherwise stated:

Melting points (m.p.) were determined on a Gallenkamp m.p. apparatus and are uncorrected. All temperatures refer to °C.

Infrared spectra were measured in chloroform-d$_1$ solutions on a FT-IR instrument. Proton Magnetic Resonance (1H-NMR) spectra were recorded at 300 MHz as solutions in chloroform-d$_1$. Chemical shifts are reported in ppm downfield ($\delta$) from Me$_4$Si, used as an internal standard, and are assigned as singlets (s), doublets (d), doublet of doublets (dd) or multiplets (m).

Column chromatography was carried out over silica gel (Merck AG Darmstadt, Germany).

Solutions were dried over anhydrous sodium sulphate.

"Petrol" refers to petroleum ether, b.p. 40°–60° C.

Methylene chloride was redistilled over calcium hydride; tetrahydrofuran was redistilled over sodium; ethyl ether was redistilled over sodium; xylene was redistilled over phosphorus pentoxide and ethyl acetate was dried over activated molecular sieves.

The following abbreviations are used in the tables and text. EA=ethyl acetate, CH=cyclohexane, P=petroleum ether 40°–60° C., THF=tetrahydrofuran, MC=methylene chloride, EE=ethyl ether. Tlc refers to thin layer chromatography on silica plates.

Intermediate 1

(3S,4R)-3-[(R)-1-(t-Butyldimethylsilyloxy)ethyl]-4-((R)-2'-(1'-oxocyclohexyl)]azetidin-2-one (1a) and (3S,4R)-3-[(R)-1-(t-Butyldimethylsilyloxy)ethyl]-4-((S)-2'-(1'-oxocyclohexyl)]azetidin-2-one (1b)

Method A

1-Trimethylsilyloxycyclohexene (11 g) was dissolved in methylene chloride (400 ml) under nitrogen. (3R,4R)-4-Acetoxy-3((R)-(t-butyldimethylsilyloxy) ethyl)-2-azetidinone (9.28 g; intermediate A) was added to the solution, the mixture stirred at 23° and trimethylsilyl trifluoromethanesulphonate (0.66 g) was added. The mixture was stirred under nitrogen for 2 hr and then poured into an ice cold 1% solution of sodium hydrogen carbonate (300 ml). The organic layer was separated, washed with water (300 ml) and brine (300 ml). The oily residue obtained, after evaporating the solvent under reduced pressure was chromatographed (gradient elution with EE/P) to give the title compound (1a; 2.6 g) as a white solid m.p. 70°–80° (t.l.c. P/EA 4/6; Rf 0.5) and the title compound (1b; 2.63 g) as a white solid m.p. 100° (t.l.c. P/EA 4/6; Rf 0.45).

Method B

A 1M solution of lithium bis(trimethylsilyl)amide in hexane (250 ml) was added to tetrahydrofuran (250 ml), the mixture stirred under nitrogen, cooled to −78° and cyclohexanone (15.2 g) was added over 20 min. The temperature was allowed to rise to −55° for 10 min and then the mixture cooled to −78° for 40 min. Intermediate A (34 g) was added and the resulting mixture stirred for 30 min at −78°. The reaction mixture was poured into a saturated ammonium chloride solution (200 ml) and the resulting mixture extracted with ethyl acetate (3×200 ml). The combined organic layers were washed with brine, dried and evaporated under reduced pressure. The oily residue was chromatographed (gradient elution with CH/EA) to give the title compound (1a; 11.6 g) as a white solid m.p. 70–80 and the title compound (1b; 12 g) as a white solid m.p. 100° C.
Using Method A (3S,4R)-3-[(R)-1-(t-butyldimethylsilyloxy)ethyl]-4((S)-6'-(1'-oxocyclohex-2'-enyl)-azetidin-2-one (1c; 12.7 g), m.p. 125° was prepared from 2-trimethylsilyloxycyclohex-1,3-diene (19.2 g) and intermediate A (14.34 g) except that the reaction time was 18 hr and the crystalline product was obtained from the oily residue by crystallisation from EE/P in place of the chromatographic purification step.

Using method B
(3S,4R)-3-[(R)-1-(t-butyldimethylsilyloxy)ethyl]-4-((S)-2'-((R)-6'-methyl-1'-oxocyclohexyl))azetidin-2-one (1d; 0.5 g) m.p. 117° and a mixture (intermediate 1e; 3.15 g) of (3R,4R)-3-[(R)-1-(t-butyldimethylsilyloxy)ethyl]-4-((S)-2'((S)-6'-methyl-1'-oxocyclohexyl))azetidin-2-one and (3R,4R)-3-[(R)-1-(t-butyldimethylsilyloxy)ethyl]-4-((R)-2'-((S) -6'-methyl-1'-oxocyclohexyl))azetidin-2-one were prepared from intermediate A (14.35 g) and 2-methyl-1-oxo-cyclohexane 13.2 g.

(3S,4R)-3-[(R)-1-(t-Butyldimethylsilyloxy)ethyl]-4-((S)-2'-(6',6'-dimethoxy-1'-cyclohexyl))azetidin-2-one (1f; 0.97 g) from intermediate A (1.8 g) and 2,2-dimethoxy-1-oxocyclohexane (2.0 g) except that the chromatography eluants were EE and P.
(3S,4R)-3-[(R)-1-(t-Butyldimethylsilyloxy)ethyl]-4-((R)-6'-(2-methoxy-1'-oxocyclohex-2'-enyl))]azetidin-2-one (1 g) and (3S,4R)-3-[(R)-1-(t-Butyldimethylsilyloxy)ethyl]-4-((S)-6'-(2'-methoxy-1'-oxo-cyclohex-2'-enyl))]azetidin-2-one (1h)

2-Methoxy-2-cyclohexenone (11.9 g) was added dropwise to a stirred mixture of anhydrous tetrahydrofuran (200 ml) and a 1M solution of lithium bis(trimethylsilyl)amide in hexane (200 ml) cooled to −78° and under nitrogen. The temperature was maintained at −78° for a further 30 min, intermediate A (15 g) added and the reaction mixture kept at −78° for an additional 15 min. The reaction mixture was poured into a cold saturated solution of ammonium chloride (100 ml) and then extracted with ether. The organic layer was washed with a cold 1% solution of hydrochloric acid (50 ml) and a cold saturated solution of sodium hydrogen carbonate, dried and then evaporated under reduced pressure. The residue was dissolved in the minimum amount of ethyl acetate and petroleum ether (200 ml) added to give the title compound (1h; 7.9 g) as a white solid m.p. 170° (t.l.c. Rf 0.25; CH/EA 4/6). The mother liquors were evaporated under reduced pressure and submitted to flash chromatography to give the title compound (1g; 2.9 g) (t.l.c. Rf 0.20; CH/EA 4/6).
(3S,4R)-3-[(R)-1-(t-Butyldimethylsilyloxy)ethyl]-4-((R)-6'-(2'-ethoxy-1'-oxocyclohex-2'-enyl))]azetidin-2-one (1i) and (3S,4R)-3-[(R)-1-(t-Butyldimethylsilyloxy)ethyl]-4((S)-6'-(2'-ethoxy-1'-oxo-cyclohex-2'-enyl)-]azetidin-2-one (1j)

A solution of 2-ethoxy-2-cyclohexenone (24 g) in anhydrous tetrahydrofuran was added to a mixture of anhydrous tetrahydrofuran (160 ml) and a 1M solution of lithium bis(trimethylsilyl)amide in hexane (200 ml) cooled to −78° and under nitrogen and with the resultant mixture kept at −78° for 1 h. A solution of intermediate A (26.3 g) in tetrahydrofuran (80 ml) was then added over 10 min. A cold saturated solution of ammonium chloride (320 ml) was added followed by a 10% solution of hydrochloric acid (70 ml). The resultant mixture was extracted with ether (3×150 ml) washed with cold 10% hydrochloric acid (50 ml), brine and then dried. Removal of the solvent under reduced pressure gave an oily residue which was purified by flash chromatography (eluants CH/EA) to give a 1:1 mixture of the title compounds (20 g) and pure title compound (1j; 1.3 g) (t.l.c. Rf 0.36; CH/EA 1/1). The mixture was dissolved in the minimum amount of ethyl acetate, diluted with cyclohexane and chilled to give the title compound (1i; 4 g) as a white solid (t.l.c. Rf 0.38; CH/EA 1/1).

Intermediate 1K (3S,4R)-3-[(R)-1-(t-Butyldimethylsilyloxy)ethyl]-4-((R)-2'-(1'-oxo-cyclohexyl)]azetidin-2-one and (3S,4R)-3-[(R)-1-(t-Butyldimethylsilyloxy)ethyl]-4-((S)-2'-(1'-oxocyclohexyl)]azetidin-2-one 1-Trimethylsilyloxycyclohexene (11 g) was dissolved in methylene chloride (400 ml) under nitrogen. (3R,4R)-4-Acetoxy-3((R)-(t-butyldimethylsilyloxy)ethyl)-2-azetidinone (9.28 g; intermediate A) was added to the solution, the mixture stirred at 23° and trimethylsilyl trifluoromethanesulphonate (0.66 g) was added. The mixture was stirred under nitrogen for 2 hr and then poured into an ice cold 1% solution of sodium hydrogen carbonate (300 ml). The organic layer was separated, washed with water (300 ml) and brine (300 ml). Evaporation of the solvent under reduced pressure gave a mixture of the title compounds as an oil.

Intermediate 2

(3S,4R)-3-[(R)-1-(t-Butyldimethylsilyloxy)ethyl]-4[(R)-2'-((S)-6'-methoxy-1'-oxocyclohexyl))]azetidin-2-one (2a) and (3S,4R)-3-[(R)-1-(t-butyldimethylsilyloxy)ethyl]-4[(R)-2'-((R)-6'-methoxy-1'-oxocyclohexyl)-]]azetidin-2-one (2b)

10% Palladium on charcoal (1.8 g) was added to a solution of intermediate (1g: 2.2 g) in ethyl acetate (200 ml) and the mixture was hydrogenated at 1 atmosphere for 2 hr. The catalyst was removed by filtration and the filtrate evaporated under reduced pressure. The oily residue was chromatographed (eluants EA/CH 9/1) to give the title compound 2a (0.6 g) (t.l.c. Rf 0.8; EA/CH 9/1) as a light yellow oil. Further elution gave the title compound 2b (1.1 g) (t.l.c. Rf 0.4; EA/CH 9/1) as an oil.

In a similar manner:
(3S,4R)-3-[(R)-1-(t-Butyldimethylsilyloxy)ethyl]-4-((S)-2'-((S)-6'-methoxy-1'-oxocyclohexyl))]azetidin-2-one (2c; 2.1 g) was obtained from intermediate 1h (2.2 g);
(3S,4R)-3-[(R)-1-(t-Butyldimethyisilyloxy)ethyl]-4((R)-2'-((S)-6'-ethoxy-1'-oxocyclohexyl))]azetidin-2-one (2d; 0.95 g) (t.l.c. Rf 0.57; eluants EA/CH 1/1) and
(3S,4R)-3-[(R)-1-(t-Butyldimethylsilyloxy)ethyl]-4-((R)-2'-((R)-6'-ethoxy-1-oxocyclohexyl))]azetidin-2-one (2e; 3 g) (t.l.c. Rf 0.35 eluants EA/CH 1/1) from intermediate 1i (4.4 g).

Intermediate 3

(3S,4R)-3-[(R)-1-(t-Butylidmethylsilyloxy)ethyl]-4-((R)-2'-(1-oxocyclohexyl))]-1-methylthioazetidin-2one Intermediate 1a (9.56 g) was dissolved in tetrahydrofuran (60 ml) under nitrogen and cooled to −78° C. Lithium bis(trimethylsilyl)amide (32.3 ml 1M solution in hexane) was added in 8 min from a dropping funnel and the reaction stirred at −78° for 30 min. Methylthio methane sulphonate (4.08 g) was added, the mixture kept at −78° for 30 min. and then warmed to −30°C. Ethyl ether (20 ml) was added and the mixture was maintained at −30° C. for 30 min and poured in to a saturated solution of ammonium chloride (100 ml). The organic layer was washed with a 1% solution of cold hydrochloric acid (2×50 ml) then with brine (50 ml). The oil obtained after evaporation of the organic solvent was chromatographed (eluants E/P) to yield the title compound (5.15 g).

IR (CDCl$_3$) $\nu_{max}$ (cm$^{-1}$) 1765 ($\beta$-lactam), 1709 (C=O), 2850 and 1300 (—S—CH$_3$) H$^1$-NMR (CDCl$_3$): 4.307 (dd), 4.22 (m), 2.992 (t), 2.61 (m), 2.46 (m), 2.395 (s), 2.407 (m), 2.105 (m), 1.935 (m), 1.70 (m), 1.49 (m), 1.19 (d), 0.86 (s), 0.064 (s), 0.048 (s).

Intermediate 4

(3S,4R)-3-[(R)-1-(t-Butyldimethylsilyloxy)ethyl]-4-((R)-2'-((S)-6'-methylthio-1'-oxocyclohexyl))]-1-methylthioazetidin-2-one A 1M solution in hexane of lithium bis(trimethylsilyl)amide (18 ml) was cooled at −78° and a solution of intermediate 3 (5.15 g) in tetrahydrofuran (20 ml) added over 4 min. The resulting mixture was stirred for 30 min the methylthiomethanesulphonate (2.27 g) was added.

The reaction mixture was kept at −78° for 30 min then at −30° C. for 10 min. Diethyl ether (50 ml) was added and the mixture was poured into a saturated solution of ammonium chloride (200 ml). The organic layer was washed with cold 1% hydrochloric acid (2×100 ml) then with brine (100 ml). The organic layer was dried, evaporated under reduced pressure and purified by flash chromatography (eluants EE/P) to obtain the title compound (3.72 g) as a yellow oil.

IR (CDCl$_3$) $\nu_{max}$ (cm$^{-1}$) 1757 ($\beta$-lactam), 1699 (C=O)

H$^1$-NMR (CDCl$_3$): 4.396 (m), 4.18 (m), 3.5 (m), 3.03 (dd), 2.42 (s), 2.2 (m), 2.068 (s), 2.1–1.6 (m), 1.47 (d), 1.21 (d), 0.86 (s), 0.077 (s), 0.065 (s).

Intermediate 5

(3S,4R)-3-[(R)-1-(t-Butyldimethylsilyloxy)ethyl]-4-((S)-2'-((R)-6'-methylthio-1'-oxocyclohexyl))-1-methylthioazetidin-2-one (5a) and (3S,4R)-3-[(R)-1-(t-Butylmethylsilyloxyethyl]-4((S)-2'-((S)-6'-methylthio-1'-oxocyclohexyl)-1-methylthioazetidin-2-one (5b)

A 1M solution in hexane of lithium bis(trimethylsilyl)amide (18 ml) was cooled at −78° under nitrogen and a solution of intermediate 1b (2 g) in tetrahydrofuran (20 ml) was added.

During the addition the temperature rose to −70°C. The reaction mixture was kept under stirring at −78° for 30 min then methylthiomethaneulsphonate (2 ml) was carefully added over 5 min. After a further 15 min under stirring the mixture was allowed to warm to −30°C. for 1 h and then diluted with anhydrous diethylether (40 ml). The mixture was poured into a saturated aqueous solution of ammonium chloride (200 ml). The organic layer was washed with a 1% cold solution of hydrochloric acid (2×50 ml) then with brine (50 ml) and dried. The organic layer was evaporated and the residue purified by flash chromatography (eluting with petroleum ether/diethylether) to give the title compound 5a (1 g). (t.l.c. Rf=0.7 eluants P/EE 3/7). Further elution gave the title compound 5b (0.84 g) as a yellow oil (t.l.c. Rf 0 0.35 eluants P/EE 3/7).

Intermediate 5a

IR (CDCl$_3$) $\nu_{max}$ (cm$^{-1}$) 1757 ($\beta$-lactam), 1725 (C=O) H$^1$-NMR (CDCl$_3$): 4.4 (dd), 4.2 (m), 3.6 (m), 2.9 (dd), 2.6 (m), 2.45 (m), 2.4 (s), 2.11 (s), 2.0–1.7(m), 1.9 (m), 1.2 (d), 0.8 (s), 0.04 (s)

Intermediate 5b

IR (CDCl$_3$) $\nu_{max}$ (cm$^{-1}$) 1755 ($\beta$-lactam), 1707 (C=O) H$^1$-NMR (CDCl$_3$): 4.31 (dd), 4.24 (m), 3.52 (m), 3.33 (dd), 2.96 (dd), 2.45 (s). 2.17 (m), 2.12 (s), 2.1–1.9 (m), 1.75 (m), 1.46 (m), 1.18 (d), 0.86 (s), 0.06 (s).

Intermediate 6

(3S,4R)-3-[(R)-1-(t-butyldimethylsilyoxy)ethyl]-4-((R)-2'-((S)-6'-methylthio-1'-oxocyclohexyl))azetidin-2-one 6a 2-Mercaptopyridine (1.63 g) and triethylamine (1.49 g) were added to a solution of intermediate 4 (5.60 g) in methylene chloride under nitrogen and cooled at 0°. The reaction mixture was stirred at 23° for 2 hrs and then poured into cold 2% hydrochloric acid (200 ml). The organic layer was separated, washed with dilute hydrochloric acid (2×200 ml) and then with water (2×200 ml). The residue obtained after evaporating the solvent was purified by flash chromatography (eluants EE/P) to give the title compound 6a (3.87 g) as a light yellow oil.

H$^1$ NMR (CDCl$_3$) ppm. H$_3$ 2.88(dd), H$_4$ 4.16(m).

In a similar manner (3S,4R)-3-((R)-1-(t-Butyldimethylsilyloxy)ethyl-4-((S)-2'-((S)-6'-methylthio-1'-oxocyclohexyl))azetidine-2-one (6b; 0.6 g) H$^1$NMR (CDCl$_3$) ppm. H$_3$ 2.70 (m) H$_4$ 3.68 (dd) was prepared from Intermediate 5b (0.84 g), and (3S,4R)-3-[(R)-1-(t-Butyldimethylsilyloxy)ethyl]-4-((S)-2'-((R)-6'-methylthio-1'-oxocyclohexyl))azetidin-2-one (6c; 0.5 g) H$^1$NMR (CDCl$_3$) ppm H$_3$ 2.73(m), H$_4$ 3.59(dd) was prepared from Intermediate 5a (0.7 g).

Intermediate 7

(3S,4R)-1-(t-butyldimethylsilyl-4-acetoxy-3[(R)-(t-butyldimethylsilyloxy)ethyl]azetidin-2-one To a stirred ice-cold solution of the (3S,4R)-4-acetoxy-3((R)-t-butyldimethylsilyloxy)ethyl)-2-azetidinone (112 g) in dichloromethane (800 ml), t-butyldimethylchlorosilane (73 g) and triethylamine (80 ml) were added. The mixture was stirred at room temperature for 20 hours then washed with water (1 l) and brine (300 ml). The organic layer was dried and evaporated to give an oil (160 g) which was dissolved in a mixture of cyclohexane/ethyl acetate (95/5) (1600 ml) and treated with silica gel (480 g). The suspension was stirred for 15 min then filtered. The solid was washed with cyclohexane/ethyl acetate (95/5:4.81) and the solvent evaporated to give the title compound (110 g) as a pale yellow oil. (Rf=0.85 Petrol/Diethyl ether=2/1)

IR(CDCl$_3$)V$_{max}$ (cm$^{-1}$): 1747(C=O)

H$^1$-NMR a (CDCl$_3$):6.14(d), 4.15(m), 3.07(dd), 2.03(s), 1.2(d), 0.9(s), 0.84(s), 0.22(s), 0.055(s), 0.35(s), 0.005(s)ppm.

Intermediate 8

(3S,4R)-1-(t-butyldimethylsilyl-3-[(R)-1-(t-butyldimethylsilyloxy)ethyl]-4-[2'-(1'-oxo-cyclohexyl)]azetidin-2-one Stannic chloride (35.4 ml) was added dropwise to stirred acetonitrile (400 ml) under nitrogen atmosphere at −40° C., a white solid formed together with white fumes which were eliminated by nitrogen flushing. The obtained suspension was allowed to rise to −10° C. then a solution of 1-trimethylsilyloxycyclohexene (60.6 ml) and of Intermediate 7 (110 g) in acetonitrile (300 ml) was added in 10 minutes. The yellow solution was stirred at 0° C. for 10 min then poured into a stirred, ice-cold, mixture of a 10% aq solution of sodium hydroxide (1 l), diethyl ether (1 l) and ice (500 g). The organic layer was separated, washed again with sodium hydroxide (500 ml) and then with a saturated solution of ammonium chloride, dried and evaporated to give a yellow solid (117.7 g). The solid was dissolved at 40° C. in isopropanol (300 ml) then cooled at room temperature, water (300 ml) was added slowly under stirring to obtain a solid which was stirred at 0° C. for 30 min then filtered, washed with a 1 to 1 mixture of isopropanol/water (100 ml) and dried under vacuum at 40° C. for 15 hr. to afford the title compound (76 g) as a mixture of 2'R and 2'S isomers in a ratio of 70% to 30% (the ratio between the two isomers was determined by HPLC using hexane/ethanol (99/1) as eluant).

Intermediate 9

(3S,4R)-1-(t-butyldimethylsilyl)-3-[(R)-1-(t-butyldimethylsilyloxy)ethyl]-4-[6'-trimethylsilyloxycyclohex-1'-enyl)]azetidin-2-one A 1M solution of lithium bis(trimethylsilyl)amide in hexane (70 ml) was added to tetrahydrofuran (150 ml), the mixture stirred under nitrogen, cooled to −70° C. and then a solution of the compound of Intermediate 8 (15.5 g) in tetrahydrofuran (70 ml) was added over 20 min. The obtained solution was stirred for 30 min then chlorotrimethylsilane (10 ml) was added over 10 min. The reaction temperature was allowed to rise to −20° C. then the mixture was poured into a saturated ammonium chloride solution (500 ml) and the resulting mixture extracted with diethyl ether (300 ml). The organic layer was washed with water (200 ml), a 2% ice-cold solution of hydrochloric acid (300 ml), aqueous solution of sodium hydrogen carbonate and brine, dried and evaporated under reduced pressure to give the title compound as a mixture of 6'R and 6'S isomers.

Intermediate 10

(3S,4R)-3-[(R)-1(t-butyldimethylsilyloxy)ethyl]-4-[(R)-[2'-((S)-6'-hydroxy-1'-oxocyclohexyl)]azetidin-2-one The compound of Intermediate 9 was dissolved at −10° C. in dichloromethane (300 ml) and treated with sodium hydrogen carbonate (2.85 g). To the obtained suspension, 3-chloroperoxybenzoic acid (8.5 g) was added portionwise over 30 min. The reaction mixture was stirred at 0° C. for 1.5 h and at room temperature for 1 h then solid sodium sulphite (5 g) was added. After stirring for 30 min the solid was filtered and washed with dichloromethane (100 ml). The organic layer was washed with a 3% aqueous sodium sulphite solution (100 ml) followed by an ice-cold 3% aqueous sodium hydrogen carbonate solution (3×150 ml) and water, dried and evaporated to give a yellow oil which was dissolved in methanol (250 ml). Potassium fluoride (6 g) was added and the obtained solution stirred at room temperature for 30 min then poured into a saturated solution of ammonium chloride (500 ml) and the resulting mixture extracted with ethyl acetate (3×200 ml). The combined organic layers were washed with brine, dried and evaporated to give a white foam (12 g). Crystallisation from a mixture of petrol and diethyl ether (8/2) (25 ml) afforded the title compound (4.4 g) as a white solid m.p. 145°-147° C.

IR(CDCl$_3$)V$_{max}$ (cm$^{-1}$): 3501(OH), 3414(NH), 1763(C=O), 1713(C=O)

H$^1$-NMR a (CDCl$_3$): 6.29(m), 4.20(m), 4.02(dd), 3.51(d), 2.93(m), 2.81(m), 2.40(m), 2.0-1.8(m), 1.73-1.6(m), 1.03(d), 0.87(s), 0.0(s)ppm.

Intermediate 11

(3S,4R)-3-[(R)-1-(t-butyldimethylsilyloxy)ethyl]-4-[(R)-2'-((S)6'-trimethylsilyloxy-1'-oxocycxlohexyl)]azetidin-2-one The compound of Intermediate 10 (4.4 g) was dissolved in dry dichloromethane (100 ml) at room temperature. Trimethylsilyl chloride (7.5 ml) followed by triethylamine (11 ml) were added and the mixture was stirred for 1 h, then poured into water (200 ml). The organic layer was separated and washed with water (2×200 ml), dried and evaporated to give a yellow oil containing traces of triethylamine. The oil was dissolved in methanol (100 ml), silica gel (10 g) added and the suspension was stirred for 1 h then filtered. The silica gel was washed with ethyl acetate (2×100 ml) and the combined organic layers evaporated under reduced pressure at 25° C. The obtained oil was dissolved with ethyl acetate (150 ml), washed with brine, dried and evaporated to give a yellow foam which was chromatographed on silica gel using a mixture of petroleum and diethyl ether (1/1) as eluant (Rf) 0.25) to afford the title compound (3.5 g) as a white foam.

IR(CDCl$_3$) V$_{max}$ (cm$^{-1}$): 3418(NH), 1755(C=O) 1717(C=O)

H$^1$-NMR a (CDCl$_3$): 5.77(s), 4.16(m), 4.01(m), 3.95(m), 3.20(m), 2.86(dd), 2.1(m), 1.4(m), 1.25(d), 0.86(s), 0.10(s), 0.07(s), 0.05(s)ppm.

Intermediate 12

(3S,4R)-3-[(R)-1-(t-butyldimethylsilyloxy)ethyl]-4-[[(R)-1'-(4-methylphenylsulfono)hydrazono]-cyclohex-2'-yl]-azetidin-2-one(12a) and (3S,4R)-3-[R)-1-(t-butyldimethylsilyloxy)ethyl]-4-[[(S)-1'-(4-methylphenylsulfono)hydrazono]-cyclohex-2'-yl]-azetidin-2-one(12b)

To a solution of intermediate (1K 12.1 g) in glacial acetic acid (120 ml) tosylhydrazide (6.9 g) was added at room temperature. The reaction was stirred for 3 hrs., then diluted with dichloromethane (250 ml) and washed with brine (2×250 ml), then with a 5% solution of sodium hydrogen carbonate until pH 7, and with brine again (2×150 ml). The organic layer was dried and the solvent evaporated under reduced pressure. The obtained foam was stirred with diethyl ether (60 ml) for 2 hrs at room temperature to give the title compound 12b as a white powder, after filtration and drying under vacuum (6 g; m.p. 187°–189° C.; t.l.c. diethyl ether Rf=0.13). IR (CDCl$_3$) V$_{max}$ (CM$^1$) 3416(N—H), 3304(NNHSO$_4$), 1753 (lactam), 1599(C=N; C=C) H$^1$-NMR (CDCl$_3$): 7.80 (d) 7.38 (bm), 7.34(d), 5.65 (bs), 4.15 (m) 3.58 (dd) 2.63(m), 2.62(m), 2.44(s), 2.3(m), 2.08(m), 1.92(m), 1.78(d), 1.4(m), 1.20(m), 1.185(d), 0.9(s), 0.077(s), 0.067(s).

The organic layer, which contained the title compound 12a in presence of a small amount of the title compound 12b (by t.l.c.), was concentrated and the residue was purified by flash chromatography (eluant dithyl ether/petroleum ether 7:3) to give the title compound 12a as a white powder (7.6 g; m.p. 95°–96° C.; t.l.c. diethyl ether Rf-0.37)

IR (CDCl$_3$)V$_{max}$ (cm$^1$) 3410(N—H), 3306(NNHSO$_2$), 1755(lactam), 1599 (C—N; C=C) H$^1$-NMR (CDCl$_3$): 7.81(d), 7.40(m), 7.33(d), 5.60(bs) 4.09(m) 4.00(m), 2.81(dd), 2.52(m), 2.44(s), 2.3(m), 2.0–1.8(m), 1.6–1.4(m), 1.04(d) 0.87(s) 0.06(s), 0.03(s).

Intermediate 13

(3S,4R)-3-[(R)-1-(t-butyldimethylsilyloxy)ethyl]-4-[(S)-3'-cyclohex-1'-enyl]azetidin-2-one A solution of the Intermediate (12a 1.12 g) in anhydrous tetrahydrofuran (20 ml) was slowly added, at −40° C., to a stirred solution of diisopropylamide (prepared from anhydrous diisopropylamine (1.35 ml) and a 1.6M solution of n-butyllithium in hexane (5.7 ml). The reaction was slowly warmed to −20°/0° C. and maintained at −20°/0° C. for 1 h. The reaction mixture was added to a precooled 5% solution of hydrochloric acid (20 ml) and extracted with ethyl acetate (2×40 ml). The organic layer was washed with a 5% solution of sodium hydrogen carbonate (20 ml) and brine (20 ml), dried and evaporated. The crude product was purified by flash chromatography (eluant diethyl ether/petroleum ether 1/1) to give the title compound as a white powder (0.45 g, m.p. 104°–06° C.; t.l.c. diethyl ether Rf=0.73) IR (CDCl$_3$) V$_{max}$ (CM$^1$) 3416(N—H), 1753 (lactam), 1603(C=C) H$^1$-NMR (CDCl$_3$): 5.82(bs),. 5.81(m), 5.60(dd), 4.14(m), 3.46(dd), 2.85(m), 2.2.4(m), 2.00(m), 1.85–1.70(m), 1.54(m), 1.27(m) 1.23(d), 0.86(s), 0.064(s), 0.054(s).

Intermediate 14

(3S,4R)-3-[(R)-1-(t-butyldimethylsilyloxy)ethyl]-4-[(1'R,2'S,3'R)-1'2'-epoxycyclohex-3'-yl]-azetidin-2-one A solution of metachloroperbenzoic acid (3.76 g; assay 55%) in dichloromethane (50 ml) was added dropwise, at 0° C., to a solution of the intermediate 13 in methylene chloride (50 ml). The solution was warmed to room temperature and stirred for 3 hrs. The reaction mixture was added to a 10% solution of sodium sulphite (50 ml), the washed with a 5% solution of sodium hydrogen carbonate (2×50 ml) and brine (50 ml). The solution was dried and the solvent was evaporated. The crude product was purified by flash chromatography (eluant ethyl acetate/cyclohexane 3/7) to obtain the title compound as a white powder (1.53 g; m.p. 134°–136° C.; t.l.c. diethyl ether Rf=0.3)IR (CDCl$_3$) V$_{max}$ (cm$^{-1}$) 3413(N—H), 1757 (Lactam) H$^1$-NMR CDCl$_3$. 5.85(bm), 4.22(m), 3.77(dd), 3.16(t), 3.12(m), 3.01(m), 2.00–1.7(m), 1.55(m), 1.4(m), 1.24(d), 1.22(m), 0.87(s), 0.67(s).

Intermediate 15

(3S,4R)-3-[(R)-1-(t-butyldimethylsilyloxy)ethyl]-4-[(R)-6'-((S)-2'-azido-1'(R)-hydroxycyclohex-6'-yl)]azetidin-2-one To a solution of the intermediate 14 (1.5 g) in methanol (150 ml) under nitrogen, magnesium sulphate heptahydrate (1.135 g) and sodium azide (0.9 g) were added. The resulting mixture was refluxed overnight, poured into water (150 ml) and extracted with dichloromethane (3×150 ml) dried and evaporated to give the title compound (1.49 g), m.p. 124°–125° C.; t.l.c. cyclohexane/ethyl acetate 3/7(Rf 0.68); IR:V$_{max}$(CDCl$_3$) 3600, 3416, 2101, 1755 cm$^1$; 1H-NMR (300 MHZ, CDCl$_3$) 6.02(bs) 4.16(m), 3.78(m), 3.72(m), 3.60(dd), 2.99(m), 2.27(bm), 2.0–1.4(m), 1.24(m), 1.28(d), 0.89(s), 0.098(s), 0.092(s)ppm.

Intermediate 16

(3S,4R)-3-[R)-1-(t-butyldimethylsilyloxy)ethyl]-4-[(R)-6'-((S)-2'-azido-1'-oxocyclohex-6'-yl)]azetidin-2-one To a mixture of pyridinium chlorochromate (6.67 g) in dry dichloromethane (50 ml), under nitrogen, a solution of the intermediate 15 in dichloromethane (200 ml) was added. The mixture was stirred at room temperature overnight, filtered through florisil and the resulting solution evaporated under reduced pressure. The oily residue was chromatographed on silica gel using a cyclohexane/ethylacetate (1/1) mixture as eluant to afford the title compound (4 g; m.p. 134°–135° C. dec; t.l.c. diethyl ether Rf 0.68); IR:V$_{max}$ (CDCl$_3$)3416, 2104, 1759, 1720cm$^1$; $^1$H-NMR (300 MHZ. CDCl$_3$) 5.77 (bs), 0.2(m), 4.04(m), 3.00(m), 2.9(m), 2.15–1.3(m), 1.21(d), 0.87(s), 0.074(s), 0.065(s)ppm.

Intermediate 17

(3S,4R)-3-[(R)-1-(t-butyldimethylsilyloxy)ethyl]-4-[(R)-6'-((S)-2'-allyloxycarbonylamino-1'-oxocyclohex-6'-yl)]azetidin-2-one The Intermediate 16 (4 g) was dissolved in ethyl acetate (300 ml), 10% palladium on charcoal (3 g) added and the mixture hydrogenated at 3 atm for 2 hrs. A further amount of the catalyst (1 g) was added and the hydrogenation was continued for 2 hrs. The mixture was filtered through a pad of celite and the resulting solution treated with allyl chloroformate (1.7 g) and pyridine (1.12 g). The reaction mixture was kept under stirring for 30 min at room temperature, then poured into a saturated aq. solution of ammonium chloride (350 ml). The organic layer was washed with a 1% solution of hydrochloric acid (2×150 ml), then with a 5% solution of sodium hydrogen carbonate (2×150 ml) and brine (200 ml), dried and evaporated in vacuo. The residue was purified by flash chromatography on a silica column, using a cyclohexane-ethyl acetate (1/1) mixture to obtain the title compound as an oil (2 g; t.l.c. cyclohexane/ethyl acetate 3/7 Rf=0.4). IR: $V_{max}$(CDCl$_3$) 3414, 1765, 1709 cm$^1$; $^1$H-NMR (300 MHZ, CDCl$_3$) 6.05(s), 5.9(m) 5.64(bd), 5.26(m), 4.56(m), 4.4–41(m), 4.05(dd), 2.9(m), 2.75(m), 2.60(m), 2.0–1.2(m), 1.02(d), 0.86(s), 0.06(s).

Intermediate 18

(3S,4R)-3-[(R)-1'-(t-Butyldimethylsilyloxy)ethyl]-4-[(1"S,2"R,6"R)-1"-hydroxy-2"-cyano-cyclohex-6"-yl]azetidin-2-one Intermediate 14 (2.4 g) was dissolved into a mixture of dimethylformamide (80 ml) and water (40 ml), potassium cyanide (1 g) was added the mixture was warmed at 60 C. for 8 hours, diluted with ether (150 ml) and washed twice with water (150 ml). The organic layer was dried and evaporated under reduced pressure to give a crude oil which was purified by flash chromatography on silica gel (eluent ether/ethyl acetate 8/2Rf=0.4) to afford the title compound (1.7 g) as a white solid.

IR(cm$^{-1}$): 3611 (OH), 3416(NH), 1755 (CO);
NMR (ppm): 6.12(bs), 4.18–4.16(m), 3.60(dd), 3.0(dd), 2.94(m), 2.74(bs), 2.0–1.87(m), 1.85–1.6(m), 1.6–15(m), 1.29(d), 0.89(s), 0.09(s).

Intermediate 19

(3S,4R)-3-[(R)-1'(t-Butyldimethylsilyloxy)ethyl]-4-[(1"R,2"R,6"R)-1"-hydroxy-2"-(allyloxycarbonylaminomethyl)cyclohex -6"-yl]azetidin-2-one Intermediate 18 (1.7 g) was dissolved in acetic acid (15 ml) and platinum dioxide (40 mgr.) was added, the mixture was hydrogenated (1 atm) for 3.5 hours then filtered on a celite pad and the solvent was evaporated under reduced pressure. The residue was redissolved with dry dichloromethane (80 ml) at 0° C., N-ethyl-piperdine (1.8 ml) and allyl chloroformate (0.55 ml) were added and the resulting mixture was stirred for 16 hrs. The solvent was evaporated under reduced pressure to give a crude material which was redissolved with ethyl acetate (100 ml) and washed twice with brine (50 ml). The organic layer was dried and evaporated under reduced pressure to give an oil which was purified by flash chromatography on silica gel (eluants cyclohexane/ethylacetate 60/40 Rf=0.5) to afford the title compound (0.7 g) as a white solid.

IR(cm$^{-1}$): 3454(NH), 3416(NH), 1751(CO), 1720(CO);
NMR (ppm) 6.32(s), 5.9(m), 5.06(t), 4.55(m), 4.18(m), 3.78–3.6(m), 3.26(m), 3.07–2.7(m), 1.89(m), 1.83–1.2(m), 1.28(d), 0.88(s), 0.1(s), 0.09(s).

Intermediate 20

(3S,4R)-3-[(R)-1'(t-Butyldimethylsilyloxy)ethyl]-4-[(2"R,6"R)-1"-oxo-2"-(allyloxycarbonylaminomethyl)-cyclohex-6"-yl]-azetidin-2-one Intermediate 19 (0.7 g) was dissolved in methylene chloride (50 ml) and pyridinium chlorochromate (1.1 g) was added under vigorous stirring. After 2.5 hours the mixture was filtered on a celite pad diluted with methylene chloride (150 ml) was washed with cold 5% hydrochloric acid (20 ml), and then with aqueous sodium hydrogen carbonate (20 ml). The organic layer was dried and evaporated under reduced pressure to give an oil which was purified by flash chromatography on silica gel (eluants cyclohexane/ethyl acetate 30/70 Rf=0.3) to afford the title compound (0.48 g) as a white sold.

IR V$_{max}$ cm$^{-1}$): 3456 and 3439 (NH), 1759 (CO), 1720 and 1718 (CO), 1603(C═C);
NMR (d ppm) 6.02(bs), 5.98 (m), 5.23(m), 5.12(bt), 4.5(m), 4.21(m), 4.05(m), 13.35(m), 2.92(bs), 2.68(m), 2.58(m), 2.1–1.55(m), 1.32–1.2(m), 1.04(d), 0.87(s), 0.06(s).

Intermediate 21

(3S,4R)-3[(R)-1-(t-Butyldimethylsilyloxy)ethyl]-4-((R)-6'-(2'-isopropoxy-1'-oxocyclohex-2'-enyl))azetidin-2-one (21a) and (3S,4R)-3[(R)-1-(t-Butyldimethylsilyloxy)ethyl]-4-((S)-6'-(2'-isopropoxy-1'-oxocyclohex-2'-enyl))azetidin-2-one (21b)

To a mixture of 1M solution of Lithium bis(trimethylsilyl)amide in hexane (486 ml) and anhydrous THF (300 ml), under inert atmosphere and cooled to −78° C., a solution of 2-isopropoxy-2-cyclohexenone (30 g) in anhydrous THF (100 ml), was added dropwise. The temperature was maintained at −78° C. for further 30', then a solution of (3R, 4R)-4-Acetoxy-3-((R)-t-Butyldimethylsilyloxy)ethyl-2-azetidinone (46.59 g) in anhydrous THF (100 ml) was added dropwise. The reaction was kept at −78° C. for 10 min then poured in to a cold saturated solution of ammonium chloride (300 ml), and extracted with diethyl ether. The organic layer, after washing with a cold 1% solution of hydrochoric acid (150 ml) and with a cold saturated solution of sodium hydrogen carbonate, dried and evaporated under reduced pressure. The yellow oily residue was treated with petroleum ether. After filtration, the title compound 21a was obtained as a white solid (8.4 g); m.p. 130° C. dec.; t.l.c. cyclohexane/ethyl acetate 4/6 Rf 0.21; IR (Nujol), V$_{max}$(Cm$^{-1}$): 3233 (NH), 1759(C═O β-lactam), 1680(C═O); H$_1$-MNR, (CDCl$_3$): 5.92(t), 575(bs), 4.29(m), 4.2(m), 2.99(dd), 2.59(m), 2.09(m) 1.9(m), 1.27(d), 1.25(d), 1.23(d), 0.86(s), 0.06(s) p.p.m.

The mother liquors were evaporated under reduced pressure and submitted to flash chromatography to obtain the title compound 21b as an oil (9.2 g; t.l.c. cyclohexane/ethyl acetate 4/6 Rf 0.21); IR (Nujol), V$_{max}$ (cm$^{-1}$) 3425(NH), 1755 (C═O p-lactam), 1684 (C═O), 1684(C═O), 1624 (C═C).

H$^1$-NMR, (CDCl$_3$): 6.35(bs), 5.95(m), 4.2(m), 3.6(dd), 2.75(m), 2.5(m), 2.44(m), 2.07(m), 1.7(m), 1.27(d), 1.25(d), 0.86(s), 0.07(s), 0.057(s) ppm.

Intermediate 22

(3S,4R)-3[(R)-1-(t-Butyldimethylsilyloxy)ethyl]-4-((R)-6'-(2'-isopropoxy-1'-hydroxycyclohex-2'-enyl))azetidin-2-one To an ice-cold solution of intermediate 21a (5.7) in methanol (100 ml) and water (30 ml), sodium borohydride (560 mg) was added in ten portions in 1.5 hrs. During the additions the pH was maintained between 5 and 7.5 with a 5% solution of hydrochloric acid. At the end dichloromethane (200 ml) and water (100 ml) were added. The organic layer, after washing with water, was dried and evaporated under reduced pressure to give the title compound 22 as a white foam (5.5 g).

Intermediate 23

(3S,4R)-3[(R)-1-(t-Butyldimethylsilyloxy)ethyl]-4-[((R)-2'-((S)-6'-isopropoxy-1'-oxocyclohexyl))]azetidin-2-one (23a) (3S,4R)-3[(R)-1-(t-Butyldimethylsilyloxy)ethyl]-4-[((R)-2'-((R)-6'-isopropoxy-1'-oxocyclohexyl))]azetidin-2-one (23b)

The intermediate 22 (5.5 g) was dissolved in ethanol (100 ml). Then 10% palladium on charcoal (0.5 g) was added and the mixture was hydrogenated at 3 atm for 4 hrs. The catalyst was filtered off and the solution was evaporated under reduced pressure. The oily residue (5 g) was dissolved in anhydrous dichloromethane (150 ml) and pyridinium chlorochromate (4.2 g) was added. The reaction mixture was stirred at 20° C. for 6 hrs, then more pyridinium chlorochromate (2.8 g) was added. The reaction was stirred for further 4 hrs. then diluted with diethyl ether (100 ml) and decanted from black gum, which was washed twice with diethyl ether. The organic solutions were combined and evaporated under reduced pressure; the oily residue was chromatographed using a mixture ethyl acetate/cyclohexane 9/1) to obtain the title compound 23a as a white solid (0.8 g; t.l.c. ethyl acetate/cyclohexane 1/1 Rf 0.5); IR(CDCl$_3$), V$_{max}$ (cm$^{-1}$): 3416(NH), 1755(C=O $\beta$ lactam), 1705(C=O ketone).

H$^1$-NMR(CDCl$_3$): 5.89(bs), 4.17(m), 3.97(m), 3.78(m), 3.53(m), 3.15(m), 2.86(dd), 2.13(m), 2.10(m), 1.8–1.4(m), 1.24(d), 1.13(d), 0.88(s), 0.08(s), 0.06(s)ppm.

Further elution gave the title compound 23b as a white solid (1 g; m.p. 121° C.; t.l.c. ethyl acetate/cyclohexane 1/1 Rf 0.28); IR(CDCl$_3$), V$_{max}$ (Cm$^{-1}$): 3416(NH), 1759(C=O $\rho$ lactam), 1722C=O).

H$^1$NMR(CDCl$_3$): 5.7(bs), 4.18(m), 4.09(m), 3.97(dd), 3.6(m), 2.8(dd) 2.55(m), 2.3(m), .2.1(m), 1.98(m), 1.8–1.6(m), 1.22(d), 1.14(d), 0.8(s), 0.07(s), 0.06(s) ppm.

Intermediate 24

(3S,4R)-3[(R)-1-(t-Butyldimethylsilyloxy)ethyl]-4-((R)-6'-(2'-cyclopentyloxy-1'-oxocyclohex-2'-enyl))azetidin-2-one (24a) and (3S,4R)-3[(R)-1-(t-Butyldimethylsilyloxy)ethyl]-4-((S)-6'-(2'-cyclopentyloxy-1'-oxocyclohex-2'-enyl))azetidin-2-one (24b)

To a mixture of a 1M solution of Lithium bis(trimethylsilyl)amide in hexane (140 ml) and anhydrous THF (70 ml) under inert atmosphere and cooled to −78°, 2-cyclophenthyloxy-2-cyclohexenone (8.5 g) dissolved in anhydrous THF (70 ml), was added.

The temperature was kept at −78° for 40 minutes, then a cooled solution of (3R,4R)-4-acetoxy-3-((R)-t-Butyldimethylsilyloxy)ethyl-2-azetidinone (11.25 g) in anhydrous THF (70 ml) was added. The reaction mixture was kept at −78° for 5 minutes then it was poured into a cooled mixture of diethyl ether (225 ml), 10% solution of hydrochloric acid (63 ml), water (180 ml) and a saturated solution of ammonium sulphate (180 ml). The organic layer was washed with 10% solution of hydrochloric acid (2×70 ml) and brine (3×70 ml), dried and evaporated under reduced pressure. The residue was chromatographed on silica gel using a mixture of cyclohexane/ethyl acetate 9/1 to 8/2 to obtain an equimolar mixture of the two title compounds 24a and 24b (6.82 g).

The title compound 24a was obtained by crystallation from THF/Petroleum 1/5 (2.1 g, m.p. 111–113; t.l.c. cyclohexane/ethyl acetate 1/1 Rf 0.29) IR (CDCl$_3$), V$_{max}$ (CM$^{-1}$): 3412 (NH); 1757 (C=O beta lactam); 1688 (C=)); 1626 (C=C).

H$^1$-NMR (CDCl$_3$): 5.85(t), 5.67(sa), 4.4(m), 4.3(dd), 4.2(m), 2.98(dd), 2.57(m), 2.50(m), 2.1(m), 1.9(m), 1.5(m), 1.22(d), 0.83(s), 0.05(s). The mother liquors were evaporated under reduced pressure to give the title compound 24b containing a small amount of the compound 24a (2.45 g; t.l.c. cyclohexane/ethyl acetate 1/1 Rf 0.29) IR (CDCl$_3$), V$_{max}$ (cm$^{-1}$): 3425 (NH), 1757 (C=O $\beta$ lactam), 1684 (C=O), 1624 (C=C). H$^1$-NMR (CDCl$_3$) 6.38(sa), 5.87(m), 4.41(m), 4.17(m), 3.60(dd), 2.75(m), 2.49(m), 1.20(m), 1.7–1.6(m), 1.235(d), 0.86(s), 0.068(s), 0.054(s).

Intermediate 25

(3S,4R)-3[(R)-1-(t-Butyldimethylsilyloxy)ethyl]-4-[((2'R,6,'S)-6'-(2'-cyclopentyloxy-1'-oxocyclohex-6'-yl))azetidin-2-one The intermediate 24b (3.2 g) was dissolved in ethyl acetate (290 ml) 10% Palladium on charcoal (1.35 g) was added and the mixture was hydrogenated at 3 atm for 1 hr. The catalyst was filtered off through a pad of celite, and the solution was evaporated under reduced pressure. The residue was chromatographed on silica gel, using a mixture of ethyl acetate/cyclohexane 9/1 to 7/3 to obtain the title compound as a white foam (1.2 g); t.l.c. cyclohexne/ethyl acetate 1/1 Rf 0.45) IR (CDCl$_3$), V$_{max}$ (cm$^{-1}$): 3418 (NH), 1755 (C=O $\beta$ lactam), 1722(C=O).

H$^1$-NMR (CDCl$_3$): 6.097(sa), 4.15(m), 4.01(m), 3.905(m), 3.67(dd), 2.69(m), 2.43–2.22(m), 2.10(m), 2.00–1.90(m), 1.83–1.50(m), 1.33(m), 1.22(d), 0.86(s), 0.075(s), 0.049(s).

Intermediate 26

2-(t-Butyldimethylsilyloxymethyl)-cyclohexanone 2-hydroxymethyl cyclohexanone (8.8 g) tert-Butyldimethylsilyl-chloride (10 g) and Imidazole (4.6 g) were dissolved in DMF (100 ml) at room temperature.

The resulting mixture was stirred for 2 hours, then poured into petroleum ether (200 ml). The organic layer was washed twice with cold 10% sodium hydrogen carbonate (60 ml), dried, evaporated under reduced pressure and purified by flash chromatography (eluants cyclohexane/ethyl acetate 95/5 Rf=0.7) to obtain the title compound (13.6 g) as a yellow oil.

IR: (V$_{max}$ cm$^{-1}$): 3670 and 1703;

NMR (d ppm): 3.96(dd), 3.555(dd), 2.47(m), 2.4–2.2(m), 2.04(m), 1.89(m), 1.65(m), 1.40(m), 0.87(s), 0.048(s), 0.044(s).

Intermediate 27

(3S,4R)-3-[(R)-1-(t-Butyldimethylsilyloxy)ethyl]-4-[(2"R,6"R)-2"-(t-Butyldimethylsilyloxymethyl)1"-oxocyclohex-6"-yl]azetidin-2-one
(3S,4R)-3-[(R)-1-(t-Butyldimethylsilyloxy)ethyl]-4-[(2"S,6"R)-2"-(t-Butyldimethylsilyloxymethyl)1"-oxocyclohex-6"-yl]azetidin-2-one 2,2,6,6-Tetramethyl piperidine (28.3 ml) was added dropwise to a stirred solution of butyl lithium 1.6M in hexane (125 ml) in dry THF (150 ml) under nitrogen and cooled at −50°. The resulting mixture was warmed at 5° C. for 10 min cooled at −78° C., and intermediate 26 (23 g) in dry THF (100 ml) was added dropwise at −70° C. After 1 hour, (3R,4R)-4-Acetoxy-3-((R)-(tert-butyldimethylsilyloxy)ethyl-2-azetidinone (27.5 g) was added and the resulting mixture was stirred for 40 min at −78° C. The reaction mixture was poured into a saturated solution of ammonium chloride (300 ml), extracted twice with ethyl acetate (250 ml), the organic layer was dried and evaporated under reduced pressure. The oil obtained was purified by flash chromatography (eluants cyclohexane/ethyl acetate 90/10 Rf=0.3) to give a mixture of the title compound (17 g) as a yellow solid.

IR: ($V_{max}$cm$^1$) 3582, 1755(CO p-lactam), 1612
NMR: (d ppm): 6.1–5.7 (bs+bs+bs). 4.18(m), 4.06(m), 3.97(m), 3.90(m), 3.51(m), 3.74(m), 2.86(m), 2.7–2.5(m), 2.40(m), 2.14(m), 2.1–1.6(m), 1.32(m), 1.24(d), 1.17(d), 0.87(s+s+s), 0.05(m).

Intermediate 28

(3S,4R)-3-[(R)-1-(t-Butyldimethylsilyloxy)ethyl]-4-((2′S)-((6′R,S)-6′-iodo-1′-oxocyclohex-2′-yl]azetidin-2-one To a stirred 1M solution of lithium bis (trimethylsilyl) amide i hexane (48.7 ml), dissolved in anhydrous THF (70 ml) cooled to −78 C. under nitrogen atmosphere a solution of intermediate 1a (7.2 g) in THF (70 ml) was added. The resulting mixture was stirred at −70 for 1.5 hrs, cooled to −78 C. and a solution of iodine (7.4 g) in anhydrous THF (20 ml) was slowly added. The reaction was stirred for further 10 min then brine (250 ml) was added at −78 C. The resulting mixture was extracted twice with ether (150 ml); the organic layer was washed twice with a saturated solution of sodium sulphite (100 ml) and with water (100 ml). The organic layer was dried, evaporated under reduced pressure and the crude material (9.5 g) was used without any further purification.

Intermediate 29

(3S,4R)-3-[(R)-1-(t-Butyldimethylsilyloxy)ethyl]-4-((2′S)-((6′S)-6′-phenylthio-1′-oxocyclohex-2′-yl)]azetidin-2-one 29a (3S,4R)-3-[(R)-1-(t-Butyldimethylsilyloxy)ethyl]-4-((2′S)-2′((6′R)-6′-phenylthio-1′-oxocyclohex-2′-yl)]azetidin-2-one 29b Thiophenol (7.424 g) was dissolved into a solution of potassium hydroxide (5.33 g) in water (740 ml) under stirring. To the resultin solution tetrabutyl ammonium bromide (1.52 g) was added followed by a solution of intermediate 28 (15.2 g) in methylene chloride (500 ml). The resulting mixture was stirred for 16 hrs. The organic layer was separated and the aqueous phase was extracted with methylene chloride. The organic layer was dried, and evaporated under reduced pressure. The residue was chromatgraphed (elutants cyclohexane/ethyl acetate 7/3) to give thiophenol (4.9 g) and a mixture (5.34 g) of the title compounds 29a and 29b and intermediate 1A. The mixture was chromatographed using petroleum ether 40–60/diethyl ether 9/1 as elutant to give title compound 29a (0.1 g) as the first eluted material and a mixture of title compounds 29a and 29b (1.1 g) as the second eluted material. The second eluted material was further purified by HPLC (silica, n-hexane/ethyl acetate 8/2, 10 ml/min, uv detection set at 275) to give the title compound 29a (0.7 g) as a white solid (m.p. 116-7 from cyclohexane) and title compound 29b (0.12 g) as a light yellow solid m.p. 65°-7°.

Title Compound 29A $^1$H-NMR (ppm) 7.4–7.2(m), 5.8 (bs); 4.13(m); 3.9(m); 3.8(m); 3.46(m); 2.75 (dd); 2.3(m); 2.2(m); 2.00(m); 1.8(m); 1.6(m); 1.18(d); 0.8(s); 0.019(s).

Title compound 29B $^1$H-NMR (ppm) 7.4–7.3(m); 5.77(bs); 4.17(m); 4.11(m); 3.95(m); 2.8(dd); 2.6(m); 2.4(m); 2.2(m); 2.00(m); 1.7(m); 1.4(m); 1.23(d); 0.86(s); 0.06(s); 0.055(s).

Intermediate 30

(3S,4R)-3-[(R)-1-(t-Butyldimethylsilyloxy)ethyl]-4-[(2′S,6′R)-2′-methoxy-1′-hydroxycyclohex-6′-yl)]azetidin-2-one To a solution of the intermediate 14 (0.1 g) in methanol (10 ml) p-toluenesesulfonic acid monohydrate (10 mg) was added at 0°. The resulting mixture was stirred at 22° for 2 hrs, poured into diethyl ether (30 ml), washed with brine (2×50 ml), dried and evaporated to give the crude title compound as a white powder (70 mg; t.l.c. diethyl ether Rf 0.20; IR (CDCl$_3$) $V_{max}$ (cm$^{-1}$) 3700, 3609, 3418, 1753; $^1$H-NMR (300 MHZ, CDCl$_3$) 5.85(bs), 4.18(m), 3.88(bm), 3.64(dd), 3.34(s), 3.30(m), 2.95(m), 1.8(m), 1.8–1.4(m), 1.27(d), 0.88(s), 0.08(s).

Intermediate 31

(3S,4R)-3-[(R)-1-(t-Butyldimethylsilyloxy)ethyl]-4-[(2′S,6′R)-2′-methoxy-1′-oxocyclohex-6′-yl)]azetidin-2-one To a solution of the intermediate 30 (70 mg) in dry dichloromethane (8 ml) a mixture of pyridiniumchlorochromate (80 ml) in dry dichloromethane was added, under nitrogen. The resulting mixture was stirred at 22° for 4 hrs, then diluted with diethyl ether (30 mg), decanted from black gum and filtered through florisil. The organic solution was evaporated under reduced pressure to give the title compound as a pale yellow powder (30 mg; t.l.c. cyclohexane/ethyl acetate 4/6 Rf 0.43); IR (CDCl$_3$), $V_{max}$ (cm$^{-1}$): 3418, 1757, 1718; $^1$H-NMR (300 MHZ, CDECl$_3$) 5.84(sa), 4.18(m), 3.99(m), 3.57(m), 3.28(s), 3.10(m), 2.876(dd), 2.24(m), 2.08(m), 1.98(m), 1.68(m), 1.56(m), 1.248(d), 0.87(s), 0.075(s), 0.063(s).

Intermediate 32

(3S,4R)-3-[(R)-1-(t-Butyldimethylsilyloxy)ethyl]-4-[(1′S,2′S,6′R)-2′-methylamino-1′-hydroxycyclohex-6′-yl]-azetidin-2-one To a solution of the intermediate 14 (5 g) in 96% ethanol (150 ml) and water (50 ml) ammonium chloride (1.67 g) and methylamine (40 wt % solution in water; 30 ml) were added. The resulting mixture was refluxed for 15 hrs, then poured into a mixture of dichloromethane (150 ml) and brine (400 ml). The aqueous layer was extracted with dichloromethane (2×120 ml) and the organic layer washed with brine (150 ml), dried and evaporated to give the title compound as a white foam (5.2 g; t.l.c. CH$_2$Cl$_2$/MeOH/NH$_4$OH 23/7/0.5 Rf 0.75); IR (CDCl$_3$) $V_{max}$ (cm$^{-1}$)3416, 1753; $^1$H-NMR (300 MHZ, CDCl$_3$) 6.26(bs), 4.20(m), 3.80(m), 3.72(dd), 3.13(m), 2.67(m), 2.49(s), 2.02(m), 1.7–1.2(m), 1.31(d), 0.91(s), 0.12(s).

Intermediate 33

(3S,4R)-3-[(R)-1-(t-Butyldimethylsilyloxy)ethyl]-4-[(1′S,2′S,6′R)-2′-(N-allyloxycarbonyl-N-methylamino)-1′-hydroxycyclohex-6′-yl]azetidin-2-one To a solution of the intermediate 32 (5.2 g) in dry dichloromethane (120 ml), under nitrogen at 0°, allyl chloroformate (2.2 ml) and 2,2,6,6-tetramethylpiperidine (3.5 ml) were added. The reaction mixture was stirred for 10 min at 0°, then diluted with dichloromethane (60 ml) and washed with a saturated aq. solution of ammonium chloride (2×100 ml), a 5% solution of sodium hydrogen carbonate (100 ml), brine (100 ml), dried, and evaporated in vacuo. The residue was purified by trituration in diethyl ether (30 ml), to obtain the title compound as a white powder (4.54 g; m.p. 159°–161°; t.l.c. dichloromethane/methanol 9/1 Rf=0.64).

IR: $V_{max}$ (CDCl3) 3414, 1753, 1688 cm$^{-1}$; $^1$H-NMR (300 MHZ CDCl3) 6.2(bs), 5.9(m), 5.2(m), 4.6(m), 4.2(m), 4.04(m), 3.87(dd), 3.8(m), 3.17(dd), 2.86(s), 2.26(m), 1.8–1.2(m), 1.30(d), 0.89(s), 0.10(s), 0.09(s).

Intermediate 34

(3S,4R)-3-[(R)-1-(t-Butyldimethylsilyloxy)ethyl]-4-[(2'S,6'R)-2'-N-allyloxycarbonyl-N-methylamino-1-'-oxocyclohex-6'-yl)]azetidin-2-one

Method A

To a solution of the intermediate 33 (1.8 g) in dry dichloromethane (50 ml) pyridiniumchlorochromate (2.2 g) was added under nitrogen. The reaction mixture was stirred at 22° for 5 hrs, then filtered through florisil, washing with ethylacetate (200 ml), and the resulting solution evaporated under pressure. The oily residue was chromatographed on silica gel, using a cyclohexane/ethylacetate 1/1 mixture as elutant to, afford the title compound as a white powder (1.0 g; m.p. 140°–142°).

Method B

To a solution of oxalyl chloride (3.35 ml) in dry dichloromethan (15 ml), under nitrogen at −70°, a solution of dimethyl sulfoxide (3.35 ml) in dry dichloromethane (40 ml) was added dropwise in 15 min. After 15 min, a solution of the intermediate 33 (4.34 g) in dry dichloromethane (35 ml) was added dropwise in 20 min and the solution was stirred at −70° for 2 hr, then triethylamine (14 ml) was added with warming to −40° in 10 min. The solution was washed with a saturated solution of ammonium chloride (2×100 ml), brine (2×100 ml), dried, and evaporated. The crude product was triturated with a mixture of petroleum ether (40 ml) and diethyl ether (10 ml) to give the title compound as a white powder (3.71 g; m.p. 140°–142°; t.l.c. diethyl ether Rf 0.3;); IR: $V_{max}$ (CDCl3) 3414, 1763, 1718, 1691 cm$^{-1}$; $^1$-H-NMR (300 MHZ, CDCl3) 6.08(bs), 5.92(m), 5.3–5.1(m), 4.55(m), 4.20(m), 4.03(dd), 2.99(m), 2.85(s), 2.66(m), 2.08–1.8(m), 1.06(bd), 0.86(s), 0.06(s) ppm.

Intermediate 35

(3S,4R)-3-[(R)-1-(t-Butyldimethylsilyloxy)ethyl]-4-[(2'S,6'R)-2'-(N-allyloxycarbonyl-N-methylamino)-1-oxocyclohex-6'-yl)-1-allyloxalyl]-azetidin-2-one To a solution of the intermediate 34 (3.77 g) in dry dichloromethane (50 ml), solid potassium carbonate (0.15 g), then allyloxalylchloride (3 ml) were added at 22°, under nitrogen. Triethylamine (6 ml) was then added dropwise over 5 min. The reaction mixture was stirred at 22° for 45 min, then washed with a saturated solution of ammonium chloride (2×90 ml), brine (2×90 ml), dried, and evaporated. The residue was chromatographed on silica gel, using a petroleum ether/diethyl ether 1/1 mixture as eluant, to afford the title compound as a colourless oil (4.0 g; t.l.c. diethyl ether Rf 0.76)

IR: $V_{max}$ (CDCl3) 1809, 1753, 1703, cm$^{-1}$; $^1$H-NMR (300 MHZ, CDCl3) 5.97(m), 5.3(m), 5.25(m), 4.79(m), 4.65(m), 4.55(m), 4.54(m), 4.30(m), 3.24(m), 2.87(m), 2.87(s), 2.2–1.8(m), 1.1(d), 0.84(s), 0.06(s)ppm.

Intermediate 36

2-(2-benzyloxyethoxy)-cyclohexanone

A mixture of dimeric 2-hydroxycyclohexanone (13.7 g), 2 benzyloxyethanol (20 g) and p-toluensulphonic acid (2 g) were dissolved in xylene (500 ml) in a round bottom flask fitted with a Dean Stark apparatus and refluxed for 10 hrs. The resulting solution was cooled, washed with sodium hydrogen carbonate (3×50 ml) dried and concentrated under reduced pressure. The crude oil was then purified by flash chromatography using cyclohexane/ethyl acetate 60/40 as eluant yielding 20 g of the title compound (Rf=0.5).

IR, CDCl3, (cm$^{-1}$): 1722 (C=O), 1603(C=C).

$^1$H-NMR, 300 MHz, CDCl3, chemical shift (ppm, TMS): 7.32(m), 4.55(dd), 3.92(m), 3.83(m), 3.64(m), 3.60(m), 2.48(m), 2.24(m), 1.93(m), 1.8–1.55(m).

Intermediate 37

(3S,4R)3-[(R)-1-(t-butyldimethylsilyloxy)ethyl]-4-[(R)2'-[(S)6'-(2-benzyloxyethoxy)-1'-oxocyclohexyl]-]azetidin-2-one 2,2,6,6-tetramethylpiperidine (12.7 g) was dropped to a solution of n-butyllithium 2.5M in hexane (33 ml) in tetrahydrofuran (150 ml) at −70 C. under a nitrogen atmosphere. The reaction mixture was then warmed to 10 C., recooled to −70 and intermediate 36 (18.72 g) was slowly added maintaining the temperature below −70 C. After the addition was completed, the solution was maintained at that temperature for 15 min and then intermediate A (11.48 g), dissolved in THF (200 ml) was added over 30 mins maintaining the temperature below −70 C. The reaction was quenched after 5 minutes using a mixture of ammonium chloride (100 ml saturated solution) and hydrochloric acid (200 ml 10% solution) and extracted with ethyl acetate. The organic layer was washed with brine, dried, concentrated under reduced pressure and purified by flash chromatography using cyclohexane/ethyl acetate 85/15 to 30/70 as eluant, title compound (2.2 g., RF=0.65).

IR, CDCl3(cm$^{-1}$): 3418(NH), 1757(C=O lactam), 1718 (C=O), 1603 (C=O).

$^1$H-NMR 300 MHz CDCl3, chemical shift (ppm, TMS): 7.32(m), 5.71 (s broad), 4.56 (s+m), 4.18(m), 3.99(m), 3.73(m), 3.6–3.5(m), 3.15(m), 2.87(dd), 2.30(m), 2.10(m), 1.80–1.50(m), 1.19(d), 0.86(s), 0.07(s+s);

Intermediate 38

(3S,4R)-3-[(R)-1-(t-butyldimethylsilyloxy)ethyl]-4-[(R)2'-[(S)6'-(2-azidoethoxy)-1'-oxocyclohexyl]]azetidin-2-one To a stirred solution of the intermediate 37 (3.7 g) in anhydrous dimethylformamide (20 ml), triphenylphosphine (2.6 g) and sodium azide (1.8 g) were added. Carbon tetrabromide 3.4 g) was then added over 10 min. After 2 hr. the resulting mixture was diluted with diethyl ether (50 ml) and washed three times with water (30 ml). The organic layer was dried and evaporated in vacuo. The residue was chromatographed on silica gel, using a ethyl acetate/cyclohexane 7/3 mixture as eluant, to afford the title compound as a colourless oil (2.6 g t.l.c. ethyl acetate/cyclohexane 9/1Rf=0.8).

IR (CDCl3 $V_{max}$ (cm$^{-1}$) 3161 (N—H), 1759 (lactam), 1707 (C=O)

H$^1$-NMR (CDCl3): 5.84 (sa), 4.18(m), 4.00(m), 3.71(t), 3.60(m), 3.49(m), 3.35(m), 3.12(m), 2.88(dd), 2.25(m), 2.20–2.00(m), 1.6(m), 1.22(d), 0.86(s), 0.06(s), 0.05(s).

Intermediate 39

(3S,4R)-3-[(R)-1-(t-butyldimethylsilyloxy)ethyl]-4-[(R)2'-[(S)6'-(2-azidoethoxy)-(R/S)-1'-hydrocyclohexyl]]azetidin-2-one To a solution of the intermediate 38 (2.6 g) in methyl alcohol (70 ml) at −10 C., sodium borohydride (0.4 g) was added in 15 min. then, after 1 hr the mixture was quenched with a saturated solution of ammonium chloride (100 ml) and ethyl acetate (2×150 ml). The organic layer was dried and evaporated to afford the title compound (2.8 g) as a mixture of two diastereoisomers (t.l.c. Rf 0.6 ethyl acetate/cyclohexane 95/5).

IR (CDCl$_3$ V$_{max}$(cm$^{-1}$) 3416 (N—H OH), 2108 (N$_3$) 1753 (lactam)

H$^1$-NMR (CDCl$_3$): 6.32(sa), 6.08(sa), 6.04(sa), 5.96(sa), 4.14(m), 4.00–3.00(m), 3.21(dd), 2.10–1.0(m), 1.32(d), 1.26(s), 0.90(s), 0.12(s).

Intermediate 40

(3S,4R)-3-[(R)-1-(t-butyldimethylsilyloxy)ethyl]-4-[(R)2'-[(S)6'-(2-allyloxycarbonlyaminoethoxy)-1'-oxocyclohexyl]]azetidin-2-one To a solution of the intermediate 39 in anhydrous tetrahydrofuran (100 ml), triphenyl phosphine (1.6 g) was added, the mixture stirred at room temperature for 36 hr. and then water (0.09 ml) was added. After 12 hr the mixture was cooled at −5 C.°, and N-ethylpiperidine (0.9 ml) and allylchloroformate (0.8 ) were added. After 3 hr the mixture was diluted with ethyl acetate (100 ml) and washed with a cooled 5% solution of hydrochloric acid (2×30 ml). The organic layer was dried, evaporated and purified on silica gel using a ethyl acetate/cyclohexane 6/4 mixture as eluant. The material so obtained was dissolved in dichloromethane (30 ml), pyridinium chlorochromate (2.6 g) was added over 40 min and the mixture was refluxed. After 4 hr the mixture was filtered on celite and washed with a cooled 5% solution of hydrochloric acid (2×20 ml). The organic layer was dried and chromatographed on silica gel, using a ethyl acetate/cyclohexane 2/8 as eulant to afford the title compound as a colourless oil (0.75 g) t.l.c. ethyl acetate/cyclohexane 9/1 Rf=0.4)

IR (CDCl$_3$ V$_{max}$ (cm$^{-1}$) 3458 and 3418(N—H) 1757(lactam), 1718(C═O), 1603(C═C).

H$^1$-NMR (CDCl$_3$): 5.92(m), 5.25(m), 5.10(sa), 4.56(m), 4.18(m), 3.98(m), 3.80–3.20(m), 3.05(m), 2.88(m), 2.40–1.10(m), 1.22(d), 0.87(s), 0.07(s), 0.06(s).

Intermediate 41

Benzyl 2-[(3S,4R)-3-[(R)-1-(t-butyldimethylsilyloxy)ethyl]-4-[(2'S,6'R)-2'-mehoxy-1''-oxocyclohex-6''-yl]azetidin-2-on-1-yl]-2-hydroxyacetate To a solution of the intermediate 2a (0.6 g) in dry toluene (5 ml) benzyl glyoxylate (0.83 g) and 3A molecular sieves were added. The resulting mixture was refluxed for 3 hrs with the use of a Dean Stark trip to remove water, then concentrated under reduced pressure. The oily residue was chromatographed on silica gel, using a cyclohexane/ethyl acetate 8/2 mixture as eluant, to afford the title compound as a mixture of two isomers (0.67 g; t.l.c. cyclohexane/ethyl acetate 1/1; Rf=0.61 and 0.72).

IR (CDCl$_3$ V$_{max}$ (cm$^{-1}$) 3490(O—H), 1753(C═O β lactam), 1713(C═O ester);

$^1$H-NMR(300 MHZ, CDCl$_3$): 7.4–7.30(m), 5.54(d) 5.46(d), 5.34(d), 5.16(d), 4.80(d), 4.21(m), 4.05(m), 4.05–3.90(m), 3.55(d), 3.53(m), 3.48(m), 3.24(s), 3.23(s), 3.2–3.0(m), 2.94–2.86(dd), 2.15–1.40(m), 1.26(d).

Intermediate 42

Ethyl 2-[(3'S,4'R)-3'-[(R)-1''-(t-butyldimethylsilyloxy)ethyl]-4'-[(2'''S,6'''R)-2'-methoxy-1'''-oxocyclohex-6'''-y-]azetidine-2'on-1'-yl]-2-hydroxyacetate To a solution of (3S,4R)-3-[(R)-1''(t-butyldimethylsilyloxy)ethyl]-4-[(2S'',6R'')-2-methoxy-1''oxocyclohex-6''-yl]azetidin-2-one (0.1 g) in dry tetrahydrofuran (5 ml), ethyl glyoxylate (0.5 g), N,N,N-triethylamine (0.02 ml) and 3A molecular sieves were added. The resulting mixture was stirred at 22° for 17 hrs, then diluted with ethyl acetate (30 ml), washed with brine (3×70 ml), dried and concentrated under vacuum. The crude product was chromatographed on silica gel, using diethyl ether/light petroleum 3/7 as eluant, to afford the title compound as a colourless oil (0.1 g) (1/1 mixture of isomers at 2 position; t.l.c. diethyl ether; Rf=0.63 nd 0.51).

IR(CDCl$_3$)V$_{max}$cm$^{-1}$; 3524(O—H), 1747(C═O β lactam), 1715(C═O ester);

EXAMPLE 1

Example 1a

Allyl(4S,8S,9R,10S,12R)-4-methylthio-10-(1-(t-butyldimethylsilyloxy)-ethyl)-11-oxo-1-azatricyclo[7.2.0.0$^{3,8}$]undec-2-ene-2-carboxylate To an ice-cold solution of intermediate 6a (3.85 g) in 200 ml of dichloromethane, potassium carbonate (3 g) was added. The mixture was stirred for 10 min, then allyl oxalylchloride (5.57 g) followed by pyridine (3.48 g) were added. The reaction mixture was stirred at 25° for 1.5 hours then diluted with dichloromethane, filtered, washed with ice-cold water and dried. Removal of the solvent gave the crude oxalimido intermediate (5.37 g) which was dissolved in dry xylene (150 ml) and treated with triethyl phosphite (9.97 g). The obtained solution was heated and refluxed for 6 hours, the solvent removed under vacuum and the residue chromatographed on silica gel using mixture of a EE/P (3/7) as eluant to afford the title compound (1.78 g) as a yellow oil. IR:V$_{max}$ (CDCl$_3$) 1772 and 1717 cm$^{-1}$; $^1$H-NMR (300 MHZ, CDCl$_3$) 6.00(m), 5.43(m), 5.26(m), 4.75(m), 4.70(m), 4.17(m), 3.41(m), 3.20(dd), 2.02(s), 1.9–1.7(m), 1.23(d), 0.88(s) and 0.080(s) ppm.

Using the same general procedure the following compounds were prepared:

Example 1b

Allyl(8R,9R,10S,12R)-10-(1-(t-butyldimethylsilyloxy)ethyl)-11-oxo-1-azatricyclo[7.2.0.0$^{3,8}$]undec-2-ene-2-carboxylate.

Example 1c

Allyl(4S,8S,9R,10S,12R)-4-ethoxy-10-(1-(t-butyldimethylsilyloxy)ethyl)-11-oxo-1-azatricyclo[7.2.0.0$^{3,}$-8]undec-2-ene-2-carboxylate.

Example 1d

Allyl(8S,9R,10S,12R)-10-(1-(t-butyldimethylsilyloxy)ethyl)-11-oxo-1-azatricyclo[7.2.0.0$^{3,8}$]undec-2-ene-2-carboxylate.

Example 1e

Allyl(4S,8R,9R,10S,12R)-4-methyl-10-(1(t-butyldimethylsilyloxy)-ethyl)-11-oxo-1-azatricyclo[7.2.0.0$^{3,8}$]undec-2-ene-2-carboxylate.

Example 1f

Allyl(4R,8R,9R,10S,12R)-4-methylthio-10-(1-(t-butyldimethylsilyloxy)-ethyl)-11-oxo-1-azatricyclo[7.2.0.0$^{3,8}$]undec-2-ene-2-carboxylate.

Example 1g

Allyl(8R,9R,10S,12R)-4,4-methylthio-10-(1-(t-butyldimethylsilyloxy)ethyl)-11-oxo-1-azatricyclo[7.2.0.0$^{3,8}$]undec-2-ene-2-carboxylate.

Example 1h

Allyl(4S,8R,9R,10S,12R)-4-methylthio-10-(1-(t-butyldimethylsilyloxy)ethyl)-11-oxo-1-azatricyclo[7.2.0.0$^{3,8}$]undec-2-ene-2-carboxylate.

Example 1i

Allyl(4S,8R,9R,10S,12R)-4-methoxy-10-(1-(t-butyldimethylsilyloxy)ethyl)-11oxo-1-azatricyclo[7.2.0.0$^{3,8}$]undec-2-ene-2-carboxylate.

Example 1j

Allyl(4R,8R,9R,10S,12R)-4-methyl-10-(1-(t-butyldimethylsilyloxy)ethyl)-11-oxo-1-azatricyclo[7.2.0.0$^{3,8}$]undec-2-ene-2-carboxylate.

Example 1k

Allyl(4S,8S,9R,10S,12R)-4-methyl-10-(1-(t-butyldimethylsilyloxy)ethyl)-11-oxo-1-azatricyclo[7.2.0.0$^{3,8}$]undec-2-ene-2-carboxylate.

Example 1l

Allyl(4R,8S,9R,10S,12R)-4-methoxy-10-(1-(t-butyldimethylsilyloxy)ethyl)-11-oxo-1-azatricyclo[7.2.0.0$^{3,8}$]undec-2-ene-2-carboxylate.

Example 1m

Allyl(8S,9R,10R,12R)-4-methoxy-10(1-(t-butyldimethylsilyloxy)-ethyl)-11-oxo-1-azatricyclo[7.2.0.0$^{3,8}$]undec-2,4-diene-2-carboxylate.

Example 1n

Allyl(8R,9R,10S,12R)-4-methoxy-10-(1-(t-butyldimethylsilyoxy)ethyl)-11-oxo-1-azatricyclo[7.2.0.0$^{3,8}$]undec-2,4-diene-2-carboxylate.

The physical characteristics for the above compounds together with modifications in the reaction conditions are given in the following table.

| Example 1 | | | | | | | | | |
|---|---|---|---|---|---|---|---|---|---|
| | Starting Intermediate | | Vol of CH$_2$Cl$_2$ | Wt. of allyloxalyl chloride | | Wt. | Wt. of K$_2$CO$_3$ | Time | Vol of Xylene | Vol of P(OEt)$_3$ |
| Ex No | No. | Wt (g) | (ml) | (g) | Base | (g) | (g) | (h) | (ml) | (ml) |
| 1a | 6a | 3.85 | 200 | 5.57 | Py | 3.48 | 3 | 1.5 | 150 | 10 |
| 1b | 1b | 5.0 | 250 | 8.8 | Py | 5.0 | 5 | 3 | 250 | 15 |
| 1c | 2d | 0.93 | 520 | 0.71 | TEA | 0.8 | 0.265 | 2.5 | 60 | 4 |
| 1d | 1a | 2.9 | 80 | 2.6 | Py | 1.5 | 2.46 | 1.5 | 100 | 5.8 |
| 1e | 1e | 6.2 | 200 | 4.4 | TEA | 1.7 | 6 | 2 | 200 | 15 |
| 1f | 6c | 0.5 | 30 | 1.0 | Py | 0.6 | 0.47 | 2 | 30 | 1.5 |
| 1g | 1f | 32.2 | 800 | 49.3 | Py | 26.3 | 22.4 | 4 | 200 | 71 |
| 1h | 6b | 0.6 | 35 | 1.5 | Py | 1.0 | 0.47 | 1.5 | 30 | 2 |
| 1i | 2c | 2.3 | 20 | 1.9 | TEA | 1.1 | 0.8 | 1 | 50 | 5 |
| 1j | 1d | 1.2 | 30 | 0.8 | TEA | 0.7 | 1.5 | 4 | 30 | 3 |
| 1k | 1e | 2.3 | 60 | 1.8 | TEA | 0.4 | 2.5 | 0.3 | 100 | 8 |
| 1l | 2b | 1.1 | 50 | 0.8 | TEA | 0.5 | 0.8 | 1.5 | 100 | 5 |
| 1m | 1g | 2.4 | 75 | 3.9 | Py | 2.1 | 3.7 | 1 | 100 | 5 |
| 1n | 1h | 2.5 | 50 | 2.1 | TEA | 12.2 | 0.8 | 1 | 100 | 5 |

| | | | | | IR (CDCl$_3$) | $^1$H-NMR (CDCl$_3$) | |
|---|---|---|---|---|---|---|---|
| Ex No | | Time (h) | Eluting Solvent | Yield (g) | β-lactam (cm$^{-1}$) | H8 (ppm) | H9 (ppm) |
| 1a | | 6 | EE/P 7:3 | 1.8 | 1772 | 3.41(m) | 4.17(m) |
| 1b | | 4 | CH/EA 3:1 | 4.2 | 1772 | 3.00(m) | 3.60(dd) |
| 1c | | 3 | CH/EA 8:2 | 210 mg | 1774 | 3.16(m) | 4.13(dd) |
| 1d | | 5.5 | CH/EA 8:2 | 1.2 | 1769 | 2.78(m) | 4.10(dd) |
| 1e | | 7 | CH/EA 9:1 | 0.4 | 1772 | 3.01(m) | 3.62(dd) |
| 1f | | 6 | P/EE 2:1 | 0.3 | 1753 | 3.40(m) | 3.65(dd) |
| 1g | | 5 | P/EE 1:1 | 27 | 1778 | 2.91(m) | 3.78(dd) |
| 1h | | 3.5 | P/EE 2:1 | 0.1 | 1772 | | |
| 1i | | 2.5 | CH/EA 9:1 | 1.3 | 1772 | 2.91(m) | 3.75(dd) |
| 1j | | 4 | P/EE 9:1 | 0.1 | 1772 | 2.91(m) | 3.64(dd) |
| 1k | | 8 | CH/EE 9:1 | 0.6 | 1772 | 3.10(m) | 4.07(dd) |
| 1l | | 5 | CH/EA | 0.3 | 1772 | 2.80(m) | 4.20(dd) |

-continued

| | | Example 1 | | | | |
|---|---|---|---|---|---|---|
| 1m | 3 | 9:1 EE/P | 1.2 | 1772 | 3.35(m) | 4.10(dd) |
| 1n | 2 | 1:1 CH/EA 8:2 | 0.7 | 1774 | 3.21(m) | 3.77(dd) |

Py = pyridine
TEA = triethylamine

EXAMPLE 2

Allyl (4S,8S,9R,10S,12R)-4-methoxy-10-(1-(t-butyldimethylsilyloxy)-ethyl)-11-oxo-1-azatricyclo [7.2.0.0$^{3,8}$]undec-2-ene-2-carboxylate Intermediate 2a (0.5 g) was dissolved in methylene chloride (20 ml), anhydrous potassium carbonate (150 mg) added and the mixture stirred under nitrogen at 23°. Ally oxalychloride (0.2 ml) was added followed by triethylamine (0.2 ml). The reaction mixture stirred for 40 min and then filtered. The filtrate was washed with water (50 ml), a 5% solution of sodium hydrogen carbonate (50 ml) then brine and dried. The solution was concentrated under reduced pressure, and the oily residue dissolved in dry Xylene (30 ml). Triethyl phosphite (2 ml) was added and the mixture heated with stirring at 140° for 3 hr. The reaction mixture was cooled, concentrated under reduced pressure and the residue chromatographed (eluants CH/EA; 8:2) to give the title compound (80 mg) as a colourless oil.

IR (CDCl$_3$) $\nu_{max}$ (cm$^{-1}$): 1772 (-lactam), 1717 (C=O), 1634 (C=C) H$^1$-NMR $\delta$(CDCl$_3$): 6.0(m), 5.45 (m), 4.98 (m), 4.74 (m), 4.22 (m), 4.15 (dd), 3.28 (s), 3.22 (m), 3.21 (m), 2.07 (m), 1.84 (m), 1.66(m), 1.6–1.2(m), 1.25 (d), 0.9 (s), 0.08 (s) ppm.

EXAMPLE 3

Allyl (8R,9R,10S,12R)-4-oxo-10-(1-(t-butyldimethylsilyloxy)-ethyl)-11-oxo-1-azatricyclo [7.2.0.0$^{3,8}$]undec-2-ene-2-carboxylate An aqueous solution of 10% oxalic acid was added with continuous magnetic stirring to a suspension of silica gel (10 g, silica gel 60, for column chromatography, 70–230 mesh) in methylene chloride (20 ml). After 2–3 min. Example 1 g (4.31 g) was added and the mixture stirred at room temperature for 2 hours. The solid phase was filtered and the solid washed with methylene chloride (200 ml). The combined methylene chloride layers were washed with a 1% aqueous sodium carbonate solution, dried and evaporated to give the title compound (3.15 g) as a yellow oil. IR:$\nu_{max}$ (CDCl$_3$) 1786, 1736 and 1696 cm$^{-1}$; $^1$H-NMR (300 MHZ, CDCl$_3$) $\delta$5.94 (m), 5.43–5.27(m), 4.75 (m), 4.20 (m), 3.95(dd), 3.34(m), 3.24 (dd), 2.6(m), 2.37 (m), 2.25–2.1 (m), 1.8–1.6 (m), 1.25 (d), 0.89 (s) and 0.08 (s) ppm.

EXAMPLE 4

Allyl (4S,8R,9R,10S,12R)-4-hydroxy-10-(1-(t-butyldimethylsilyloxy)-ethyl)-11-oxo-1-azatricyclo [7.2.0.0$^{3,8}$]undec-2-ene-2-carboxylate To an ice-cold solution of Example 3 (1 g) in methanol (20 ml) and water (10 ml), sodium borohydride (180 mg) was added in 5 portions over 10 min. During the additions the pH was maintained between 4 and 7 with diluted hydrochloric acid (1%). Dichloromethane (100 ml) and water (100 ml) were then added, the organic layer separated, washed with water, dried and evaporated to give the title compound (980 mg) as a white oil. IR:$\nu_{max}$ (CDCl$_3$) 1774 and 1693 cm$^{-1}$; $^1$NHR (300 MHZ, CDC$_3$) $\delta$6.21 (s), 5.94 (m), 5.45 (m), 5.28 (m), 4.77 (m), 4.41 (m), 4.17 (m), 3.70 (dd), 2.93 (m), 2.22 (m), 2.09 (m), 1.42 (m), 1.22 (dd), 0.88 (s), 0.07 (s) ppm.

EXAMPLE 5

Example 5a

Allyl (4S,8S,9R,10S,12R)-4-methylthio-10-(1-hydroxyethyl)-11-oxo-1-azatricyclo [7.2.0.0$^{3,8}$]undec-2-ene-2-carboxylate To an ice-cold solution of Example 1a (1.75 g) in dry tetrahydrofuran (70 ml), acetic acid (2.32 g) and tetrabutylammonium fluoride (3.05 g) (11.7 ml of solution 1.0M in THF) were added. The mixture was stirred at 25° C. for 20 hours then diluted with diethylether (250 ml) and washed with a 2% aqueous sodium bicarbonate solution, ice water and brine. The organic layer was dried and evaporated under vacuum to give a thick oil which was chromatographed on silica gel using an EE/P (7/3) mixture as eluant to afford the title compound as a yellow oil (0.52 g). IR:$\nu_{max}$ (CDCl$_3$) 1772 and 1720 cm$^{-1}$; $^1$H-NMR (300 MHZ CDCl$_3$) $\delta$5.96 (m), 5.43 (dq), 5.27 (dq), 4.80(m), 4.67(m), 4.21 (dd), 4.20 (m), 3.48 (m), 3.25 (dd), 2.01 (s), 2.10–1.60 (m), 1.50–1.30 (m) and 1.32 (d) ppm.

The following compounds were prepared using the same general procedure.

Example 5b

Allyl (8R,9R,10S,12R)-10-(1-hydroxyethyl)-11-oxo-1-azatricyclo [7.2.0.0$^{3,8}$]undec-2-ene-2-carboxylate

Example 5c

Allyl (4S,8S,9R,10S,12R)-4-ethoxy-10-(1-hydroxyethyl)-11-oxo-1-azatricyclo [7.2.0.0$^{3,8}$]undec-2-ene-2-carboxylate

Example 5d

Allyl (8S,9R,10S,12R)-10-(1-hydroxyethyl)-11-oxo-1-azatricyclo [7.2.0.0$^{3,8}$]undec-2-ene-2-carboxylate

Example 5e

Allyl (4S,8R,9R,10S,12R)-4-methyl-10-(1-hydroxyethyl)-11-oxo-1-azatricyclo [7.2.0.0$^{3,8}$]undec-2-ene-2-carboxylate

Example 5f

Allyl (4R,8R,9R,10S,12R)-4-methylthio-10-(1-hydroxyethyl)-11-oxo-1-azatricyclo [7.2.0.0$^{3,8}$]undec-2-ene-2-carboxylate

Example 5g

Allyl (4S,8R,9R,10S,12R)-4-hydroxy-10-(1-hydroxyethyl)-11-oxo-1-azatricyclo[7.2.0.0$^{3,8}$]undec-2-ene-2-carboxylate

Example 5h

Allyl (4S,8R,9R,10S,12R)-4-methylthio-10-(1-hydroxyethyl)-11-oxo-1-azatricyclo [7.2.0.0³,⁸]undec-2-ene-2-carboxylate

Example 5i

Allyl (4S,8R,9R,10S,12R)-4-methoxy-10-(1-hydroxyethyl)-11-oxo-1-azatricyclo [7.2.0.0³,⁸]undec-2-ene-2-carboxylate

Example 5k

Allyl (4S,8S,9R,10S,12R)-4-methyl-10-(1-hydroxyethyl)-11-oxo-1-azatricyclo [7.2.0.0³,⁸]undec-2-ene-2-carboxylate

Example 5l

Allyl (4R,8S,9R,10S,12R)-4-methoxy-10-(1-hydroxyethyl)-11-oxo-1-azatricyclo [7.2.0.0³,⁸]undec-2-ene-2-carboxylate

EXAMPLE 7

Example 7a

Allyl (4S,8S,9R,10S,12R)-4-methylsulfinyl-10-(1-hydroxyethyl)-11-oxo-1-azatricyclo [7.2.0.0³,⁸]undec-2-ene-2-carboxylate To a solution of the Example 5a (0.15 g) in dry dichloromethane (30 ml) at −78° C., 3-chloroperoxybenzoic acid (0.77 g) in dichloromethane (10 ml) was added dropwise over 15 minutes. The mixture was stirred at −78° C. for 1 hour then washed with a 3% aqueous sodium sulphite solution followed by an ice-cold 3% aqueous sodium hydrogen carbonate solution and water. The organic layer was dried and evaporated to give the title compound as a clear oil (0.10 g). IR:$\nu_{max}$(CDCl$_3$) 1778, 1717 and 1040 cm$^{-1}$. $^1$H-NMR (300 MHZ, CDCl$_3$) δ5.96 (m), 5.35 (m), 4.77 (m), 4.23 (m), 3.29 (m), 3.10 (m), 2.68–2.55 (m), 2.58 (s), 2.2–1.6 (m), 1.5–1.4(m) and 1.30 (d) ppm.

Using the general method described above but with a reaction temperature of −40° C.

Allyl (4S, 8R,9R,10S,12R)-4-methylsulfinyl-10-(1-hydroxyethyl)-11-oxo-1-azatricyclo [7.2.0.0³,⁸]undec-2-carboxylate. (7B) 113 mg was prepared from example 5 h (190 mg) and 3-chloroperoxybenzoic acid (96 mg).

EXAMPLE 8

Example 8a

Potassium (4S,8S,9R,10S,12R)-4-methylthio-10-(1-hydroxyethyl)-11-oxo-1-azatricyclo [7.2.0.0³,⁸]undec-2-ene-2-carboxylate To a solution of Example 5a (500 mg) and triphenylphosphine (78 mg) in a mixture of dry dichloromethane (3 ml) and ethyl acetate (3 ml), was added a solution of potassium 2-ethylhexanoate (246 mg) and tetrakis(triphenylphosphine) palladium (86 mg) in dichloromethane (4 ml). The mixture was stirred for 30 minutes then diethylether (25 ml) was added and the obtained solid filtered, washed with diethylether and dried to give the title compound (400 mg) as a yellow solid IR:$\nu_{max}$ (Nujol) 1749, 1701 and 1589 cm$^{-1}$; $^1$H-NMR (300 MHZ, D$_2$O-Acetone) s 4.53 (m), 4.06 (m), 4.02 (m), 3.24

Example 5

| | Starting Intermediate | | Wt. of TBAF | Wt. of AcOH | Vol. of THF | Time | Eluting | Yield | IR (CDCl$_3$) β-lactam | $^1$H-NMR (CDCl$_3$) | |
|---|---|---|---|---|---|---|---|---|---|---|---|
| Ex No | No. | Wt (mg) | (g) | (g) | (ml) | (h) | Solvent | (mg) | (cm$^{-1}$) | H8 (ppm) | H9 (ppm) |
| 5a | 1a | 3.05 | 1.75 g | 3.05 | 2.23 | 70 | EE/P 7:3 | 520 | 1772 | 3.48(m) | 4.2(dd) |
| 5b | 1b | 900 | 1.80 | 1.40 | 30 | 20 | EE/P 3:1 | 300 | 1772 | 2.86(m) | 3.69(dd) |
| 5c | 1c | 220 | 0.16 | 0.26 | 20 | 48 | CH/EA 9:1 | 20 | 1771 | 3.25(m) | 4.14(dd) |
| 5d | 1d | 1.02 g | 1.96 | 1.51 | 30 | 24 | EA/CH 8:2 | 380 | 1769 | 2.80(m) | 4.15(dd) |
| 5e | 1e | 220 | 0.54 | 0.52 | 7 | 16 | CH/EA 7:3 | 110 | 1771 | 3.05(m) | 3.69(dd) |
| 5f | 1f | 250 | 0.47 | 0.35 | 7 | 24 | EE | 60 | 1771 | 3.43(m) | 3.72(dd) |
| 5g | 10 | 1 g | 2.50 | 1.42 | 30 | 20 | EE | 320 | 1774 | 2.97(m) | 3.76(dd) |
| 5h | 1h | 400 | 0.70 | 0.44 | 10 | 18 | EE | 110 | 1771 | 3.06(m) | 3.75(dd) |
| 5i | 1i | 800 | 2.35 | 1.15 | 50 | 24 | EA/CH 1:1 | 430 | 1774 | 2.94(m) | 3.80(dd) |
| 5j | 1j | 500 | 2.18 | 1.05 | 25 | 24 | CH/EA 1:1 | 180 | 1772 | 2.93(m) | 3.69(dd) |
| 5k | 1h | 400 | 0.78 | 0.84 | 20 | 16 | CH/EA 1:1 | 100 | 1769 | 3.10(m) | 4.13(dd) |
| 5l | 1i | 270 | 0.81 | 0.40 | 30 | 24 | CH/EA 6:4 | 80 | 1772 | 2.83(m) | 4.20(dd) |

EXAMPLE 3

Allyl (4S, 8S, 9R, 10S, 12R)-4-methoxy-10-(1-hydroxy)ethyl)-11-oxo-1-azatricyclo [7.2.0.0³,⁸]undec-2-ene-2-carboxylate Example 2 (80 mg) was dissolved in dry tetrahydrofuran (2 ml), acetic acid (0.09 ml) was added followed by a 1M solution of tetrabutylammonium fluoride in tetrahydrofuran (0.45 ml). The reaction was stirred at 23° C. for 48 h then diluted with ethyl acetate (50 ml), extracted with a 5% solution of sodium hydrogen carbonate (2×50 ml) then with brine (50 ml). The residue after evaporation was purified by flash chromatography (eluants CH/EA mixtures) to obtain the title compound 20 mg as an oil.

IR (CDCl$_3$) $\nu_{max}$ (cm$^{-1}$): 3609 (O—H), 1772 (lactam), 1717 (C=O), 1642 (C=C)

H$^1$-NMR s (CDCl$_3$): 5.96 (m), 5.43 (m), 5.27 (m), 4.96 (m), 4.82 (m), 4.68 (m), 4.237 (m), 4.19 (dd), 3.25 (s), 3.28 (m), 3.20 (m), 2.08 (m), 1.9–1.8 (m), 1.65 (m), 1.45 (m), 1.32 (d) ppm.

(m), 3.18 (m), 1.83 (s), 1.85–1.50 (m), 1.4–1.2(m) and 1.10 (d) ppm.

Using the above general procedure the following compounds have been prepared and specific details are given in the table.

Example 8b

Potassium (8R,9R,10S,12R)-10-(1-hydroxyethyl)-11-oxo-1-azatriciclo [7.2.0.0$^{3,8}$]undec-2-ene-2-carboxylate.

Example 8c

Potassium (4S,8S,9R,10S,12R)-4-ethoxy-10-(1-hydroxyethyl)-11-oxo-1-azatriciclo [7.2.0.0$^{3,8}$]undec-2-ene-2-carboxylate.

Example 8d

Potassium (8S,9R,10S,12R)-10-(1-hydroxyethyl)-11-oxo-1-azatriciclo [7.2.0.0$^{3,8}$]undec-2-ene-2-carboxylate.

Example 8e

Potassium (4S,8R,9R,10S,12R)-4-methyl-10-(1-hydroxyethyl)-11-oxo-1-azatriciclo[7.2.0.0$^{3,8}$]undec-2-ene-2-carboxylate.

Example 8f

Example 8i

Potassium (4S,8R,9R,10S,12R)-4-methoxy-10-(1-hydroxyethyl)-11-oxo-1-azatriciclo [7.2.0.0$^{3,8}$]undec-2-ene-2-carboxylate.

Example 8j

Potassium (4R,8R,9R,10S,12R)-4-methyl-10-(1-hydroxyethyl)-11-oxo-1-azatriciclo [7.2.0.0$^{3,8}$]undec-2-ene-2-carboxylate.

Example 8k

Potassium (4S,8S,9R,10S,12R)-4-methyl-10-(1-hydroxyethyl)-11-oxo-1-azatriciclo [7.2.0.0$^{3,8}$]undec-2-ene-2-carboxylate.

Example 8l

Potassium (4R,8S,9R,10S,12R)-4-methoxy-10-(1-hydroxyethyl)-11-oxo-1-azatriciclo [7.2.0.0$^{3,8}$]undec-2-ene-2-carboxylate.

Example 8m

Potassium (4S,8R,9R,10S,12R)-4-methlsulfinyl-10-(1-hydroxyethyl)-11-oxo-1-azatriciclo [7.2.0.0$^{3,8}$]undec-2-ene-2-carboxylate.

Example 8

| Ex No | Starting Material Ex. No. | Wt (mg) | Wt. of PPH$_3$ (mg) | Wt. of a K+ (g) | Wt. of Pd(Ph$_3$)$_4$ (mg) | Solvent | Vol. (ml) | Time (min) | Vol. of Diethyl-ether (ml) | Yield (mg) | IR (Nujol) B-lactam (cm$^{-1}$) | $^1$H-NMR (D$_2$O-Acetone) H8 | H9 (ppm) |
|---|---|---|---|---|---|---|---|---|---|---|---|---|---|
| 8a | 5a | 500 | 78 | 246 | 85 | MC/EA 1:1 | 6 | 30 | 25 | 400 | 1749 | 3.18(m) | 4.02(m) |
| 8b | 5b | 35 | 6 | 25 | 9 | MC/EA 1:1 | 2 | 10 | 5 | 10 | 1778 | 2.75(m) | 3.50(m) |
| 8c | 5c | 50 | 4 | 25 | 5.2 | MC/EA 2:3 | 5 | 60 | 5 | 6 | 1738 | 3.13(m) | 4.11(dd) |
| 8d | 5d | 200 | 36 | 127 | 48 | MC/EA 1:1 | 5 | 30 | 10 | 112 | 1755 | 2.70(m) | 4.06(dd) |
| 8e | 5e | 100 | 10 | 60 | 10 | MC/EA 1:1 | 5 | 5 | 5 | 60 | 1751 | 3.00(m) | 3.49(dd) |
| 8f | 5f | 70 | 9 | 45 | 14 | MC/EA 1:1 | 2 | 45 | 10 | 40 | 1753 | 3.15(m) | 3.52(dd) |
| 8g | 5g | 280 | 52 | 230 | 63 | THF | 7 | 10 | 10 | 110 | 1767 | 2.95(m) | 3.54(dd) |
| 8h | 5h | 100 | 9 | 72 | 15 | MC/EA 1:1 | 4 | 30 | 7 | 20 | 1742 | 2.91(m) | 3.59(dd) |
| 8i | 5i | 200 | 20 | 182 | 15 | MC/EA 2:1 | 6 | 30 | 2 | 30 | 1751 | 2.84(m) | 3.62(dd) |
| 8j | 5j | 150 | 13.5 | 88 | 20 | MC/EA 1:1 | 10 | 10 | 10 | 120 | 1751 | 2.75(m) | 3.53(dd) |
| 8k | 5k | 100 | 9 | 58 | 13 | MC/EA 1:1 | 6 | 240 | 10 | 60 | 1751 | 2.97(m) | 3.90(dd) |
| 8l | 5l | 80 | 15 | 45 | 8 | MC/EA 1:1 | 2 | 60 | 3 | 65 | 1751 | 2.68(m) | 4.05(m) |
| 8m | 5m | 90 | 6 | 54 | 15 | MC/EA 1:1 | 4 | 30 | 5 | 40 | 1751 | 2.93(m) | 4.04(dd) |

Potassium (4R,8R,9R,10S,12R)-4-methylthio-10-(1-hydroxyethyl)-11-oxo-1-azatriciclo [7.2.0.0$^{3,8}$]undec-2-ene-2-carboxylate.

Example 8g

Potassium (4S,8R,10S,12R)-4-hydroxy-10-(1-hydroxyethyl)-11-oxo-1-azatriciclo [7.2.0.0$^{3,8}$]undec-2-ene-2-carboxylate.

Example 8h

Potassium (4S,8R,9R,10S,12R)-4-methylthio-10-(1-hydroxyethyl)-11-oxo-azatriciclo [7.2.0.0$^{3,8}$]undec-2-ene-2-carboxylate.

EXAMPLE 9

Potassium (4S,8S,9R,10S,12R)-4-methoxy-10-(-1-hydroxyethyl)-11-oxo-1-azatriciclo[7.2.0.0$^{3,8}$]undec-2-ene-2-carboxylate Example 6 (17 mg) was dissolved in dry tetrahydrofuran (2 ml) and to this was added a solution formed from a 0.5 molar solution of potassium 2-ethylhexanoate in ethyl acetate (0.1 ml), palladium (tetrakis)triphenylphosphine (5 mg) and triphenylphosphine (3 mg) in tetrahydrofuran (1.5 ml). The reaction was stirred at 23° C. for 20' and then diluted with a 1/1 mixture of ethyl ether and petroleum ether. The solid obtained was filtered, washed with ethyl ether/petroleum ether mixtures and dried to give the title compound (5 mg) as a white solid.

IR (CDCl$_3$) $\nu_{max}$ (cm$^{-1}$): 1751 (-lactam), 1589 (C=O)

H$^1$-NMR δ(CDCL$_3$): 4.76 (m), 4.07 (m), 4.03 (m), 3.26 (dd), 3.08 (s), 2.99 (m), 1.84 (m), 1.71 (m), 1.53 (m), 1.41 (m), 1.2(m), 1.11 (d) ppm.

EXAMPLE 10

Potassium (4S,8S,9R,10S,12R)-4-methylsulfinyl-10-(1-hydroxyethyl)-11-oxo-1-azatricyclo [7.2.0.0$^{3,8}$]undec-2-ene-2-carboxylate To a solution of Example 7a (160 mg) and triphenylphosphine (9 mg) in 4 ml of a mixture 1/1 of dry dichloromethane and ethyl acetate, potassium 2-ethylhexanoate (80 mg) and tetrakis(triphenylphosphine) palladium (20 mg) were added. The mixture was stirred for 45 minutes, then dry diethyl ether (5 ml) was added. The obtained solid filtered, washed with diethyl ether and dried to give the title compound (25 mg) as yellow solid. IR:$\nu_{max}$ (Nujol) 1751 cm$^{-1}$; $^1$H-NMR δ(D$_2$O-Acetone): 4.6 (m), 4.07 (m), 4.04(dd), 3.34 (dd), 2.93 (m), 2.50 (s), 2.22–1.6(m), 1.27 (m) and 1.09 (d) ppm.

EXAMPLE 11

Allyl(4S,8S,9R,10S,12R)-4-trimethylsilyloxy-10-[1-(t-butyldimethylsilyloxy)-ethyl]-11-oxo-1-azatricyclo[7.2.0.0$^{3,8}$]undec-2-ene-2-carboxylate To an ice-cold solution of the compound of Intermediate 11 (2.7 g) in dichloromethane (50 ml) potassium carbonate (1.8 g) was added. The mixture was stirred for 10 min, then triethylamine (2.7 ml) was added. Allyloxalychloride dissolved in dichloromethane (5 ml) was added dropwise over 15 min and the reaction mixture was stirred for 1 hour then filtered, washed with water (3×200 ml) and dried, Removal of the solvent gave the crude oxalimido intermediate which was dissolved in dry xylene (50 ml) and treated with triethyl phosphite (6.7 ml). The obtained solution was heated and refluxed for 3.5 hours, the solvent removed under vacuum and the residue chromatographed on silica gel using a mixture of petroleum and diethyl ether (8/2) as eluant to afford the title compound (1.6 g) as a yellow oil.

IR (CDCl$_3$) V$_{max}$ (cm$^{-1}$): 1771(C=O), 1751(C=O), 1634(C=C)

H$^1$-NMR a (CDCl$_3$): 5.96(m), 5.44(m), 5.4(m), 4.72(m), 4.18(m), 4.08(dd), 3.28(m), 3.145(dd), 2.0–1.75(m), 1.6(m), 1.41(m), 1.32(m), 1.23(d), 0.8(s), 0.09–0.06(s)ppm.

EXAMPLE 12

Allyl(4S,8S,9R,10S,12R)-4-hydroxy-10-[1-(t-butyldimethylsilyloxy)-ethyl]-11-oxo-1-azatricyclo[7.2.0.0$^{3,}$ $^8$]undec-2-ene-2-carboxylate The compound of Example 11 (1.4 g) was dissolved in tetrahydrofuran (20 ml) and the mixture stirred at 0° C. Acetic acid (05 ml) was added followed by 1.1M solution of tetrabutylammonium fluoride in tetrahydrofuran (2.8 ml). The reaction was stirred at 0° C. for 45 min then some more acetic acid (0.5 ml) and tetrabutylammonium fluoride in tetrahydrofuran (1 ml) were added. The reaction was stirred for 45 min then poured into a stirred, ice-cold, mixture of diethyl ether (150 ml) and a 2.5% aqueous solution of sodium bicarbonate (100 ml). The organic layer was washed with water (2×200 ml), brine dried and evaporated to give the title compound (1.1 g) as a clear oil. IR(CDCl$_3$) V$_{max}$ (cm$^{-1}$): 1772(C=O), 1717(COO), 1634(C=C)

H$^1$-NMR a (CDCl$_3$): 5.94(m), 5.48(m), 5.43(m), 5.25(m), 4.73(m), 4.20(m), 4.14(dd), 3.36(m), 3.19(dd), 2.3(m), 2.1–1.8(m), 0.165(m), 1.51(m), 1.4(m), 1.23(d), 0.88(s), 0.07(s)ppm.

EXAMPLE 13

Allyl(4S,8S,9R,10S,12R)-4-methoxy-10-[1-(t-butyldimethylsilyloxy)-ethyl]-11-oxo-1-azatricyclo[7.2.0.0$^{3,}$ $^8$]undec-2-ene-2-carboxylate The compound of Example 12 (1 g) was dissolved in diethyl ether (100 ml) under nitrogen and cooled at −78° C. Methyl trifluoromethanesulfonate (0.54 ml) was added then potassium bis(trimethylsilyl)amide (7.8 ml), 05M solution in toluene) was added dropwise over 2 hours, at the end some more methyl trifluoromethanesulphonate (0.3 ml) was added followed by a dropwise addition of potassium bis(trimethylsilyl)amide (4 ml, 0.5M in toluene). After 1 hour the reaction mixture was poured into a saturated solution of ammonium chloride (300 ml) and separated. The organic layer was washed with a 1% solution of cold hydrochloric acid (2×200 ml), water and brine, dried and evaporated. The oily residue was chromatographed on silica gel using a mixture of petroleum and diethyl ether (7/3) as eluant to afford the title compound (370 mg) as a colourless oil (Rf 0.45).

IR(CDCl$_3$) V$_{max}$ (cm$^{-1}$): 1772(C=O), 1717(COO), 1634(C=C) $^1$H-NMR a (CDCl$_3$): 6.0(m), 5.45(m), 4.98(m), 4.74(m), 4.22(m), 4.15(dd), 3.28(s), 3.22(m), 3.21(m), 2.07(m), 1.84(m), 1.66(m), 1.6–1.2(m), 1.22(d), 0.9(s), 0.08(s)ppm.

EXAMPLE 14

Allyl(4S,8S,9R,10S,12R)-4-methoxy-10-(1-hydroxyethyl)-11-oxo-1-azatricyclo[7.2.0.0$^{3,8}$]undec- 2-ene-2-carboxylate The compound of Example 13 (370 mg) was dissolved in dry tetrahydrofuran (12 ml) acetic acid (0.5 ml) was added followed by a 1.1M solution of tetrabutylammonium fluoride in tetrahydrofuran (2.85 ml). The reaction was stirred at room temperature for 30 hours then diluted with ethyl acetate (200 ml), washed with a 5% solution of sodium hydrogen carbonate (2×200 ml) then with brine, dried and evaporated to give a yellow oil which was purified by chromatography using diethyl ether as eluant (Rf 0.4) to obtain the title compound (180 mg) as a white oil.

IR(CDCl$_3$) V$_{max}$ (cm$^{-1}$): 3609(OH), 1772(C=O), 1717(COO), 1642(C=C)

H$^1$-NMR S (CDCl$_3$): 5.96(m), 5.43(m), 5.27(m), 4.96(m), 4.82(m), 4.68(m), 4.237(m), 4.19(dd), 3.25(s), 3.28(m), 3.20(m), 2.08(m), 1.9–1.8(m), 1.65(m), 1.45(m), 1.32(d)ppm.

EXAMPLE 15

Potassium(4S,8S,9R,10S,12R)-4-methoxy-10-(1-hydroxyethyl)-11-oxo-1-azatricyclo [7.2.0.0$^{3,8}$]undec-2-ene-2-carboxylate To a solution of the compound of Example 14 (420 mg) and triphenylphospine (15 mg) in dry tetrahydroduran, a solution of tetrakis(triphenylphosphine)palladium (30 mg) in tetrahydrofuran (2 ml) and a 0.5M solution of potassium 2-ethylexanoate (3 ml) were quickly added. The reaction mixture was stirred for 30 min then the obtained white solid was centrifugated, washed with a mixture of diethyl ether and tetrahydrofuran (8/2) (3×10 ml) and diethyl ether (2×10 ml) then dried under vacuum to give the title compound (400 mg).

IR(Nujol) $V_{max}$ (cm$^{-1}$): 3609(OH), 1772(C=O), 1717(COO), 1642(C=C)

H$^1$-NMR S (D$_2$O-Acetone): 4.6(m), 4.07(m), 4.04(dd), 3.34(dd), 2.93(m), 2.50(s), 2.22–1.6(m), 1.27(m), 1.09(d)ppm.

EXAMPLE 16

Allyl(4S,8S,9R,10S,12R)-4-allyloxycarbonylamino-10-[1-(t-butyldimethylsilyloxy)-ethyl]-11-oxo-1-azatricyclo[7.2.0.0$^{3,8}$]undec-2-ene-2-carboxylate To an ice cold solution of Intermediate 17 (2 g) in anhydrous dichloromethane (100 ml), solid potassium carbonate (0.680 g) was added. The mixture was stirred for 30 min., then allyloxalylchloride (0.88 g) followed by triethylamine (0.59 g) were added. The reaction mixture was stirred at room temperature for 1 hr, then further allyloxalylchloride (0.88 g) and triethylamine (0.59 g) were added. After 15 min the reaction mixture was diluted with dichloromethane, filtered, washed with 5% hydrochloric solution, 5% sodium hydrogen carbonate solution, and brine. Removal of the solvent gave the crude oxalimido intermedidate which was dissolved in dry xylene (130 ml) and treated with triethylphosphite (7.4 ml). The obtained solution was heated at reflux for 2½ hrs., the solvent removed under vacuum and the residue chromatographed on silica gel using a mixture of diethylether/petroleum (9/1) as eluant to afford the title compound as a yellow oil (1.7 g); IR:- $V_{max}$ (CDCl$_3$) 3425, 1769, 1742, 1649 cm$^1$;

$^1$H-NMR (300 MHZ, CDCl$_3$) 6.05–5.8(m), 5.45(t), 5.5–5.18(m), 4.96(d), 4.78(m), 4.55(m), 4.19(m), 4.12(dd), 3.16(dd), 3.06(m), 1.97(m), 1.9–1.5(m), 1.4–1.2(m), 1.23(d), 0.88(s), 0.07(s).

EXAMPLE 17

Allyl(4S,8S,9R,10S,12R)-4-allyloxycarbonylamino-10-(1-hydroxyethyl)-11-oxo-1-azatricyclo[7.2.0.0$^{3,8}$]undec-2-ene-2-carboxylate To an ice cold solution of Example 16 (0.98 g) in dry tetrahydrofuran (60 ml), acetic acid (0.93 g) and solid tetrabutylammonium fluoride trihydrate (1.83 g) were added. The mixture was stirred at room temperature for 30 hrs., then poured into water and extracted with ethyl acetate (3×180 ml). The organic layer was washed with 5% sodium hydrogen carbonate solution and brine, dried and evaporated under vacuum. The residue was chromatographed on silica gel using a mixture of methylene chloride/methanol (9/1) as eluant to give the title compound as a white foam (0.4 g); IR:V$_{max}$ (CDCl$_3$)3447, 1772, 1718 cm$^1$;

$^1$H-NMR (300 MHZ, CDCl$_3$) 6.05–5.8(m), 5.45–5.39(bt), 5.4–5.15(m), 4.94(m), 4.9–4.6(m), 4.54(m), 4.21(m), 4.16(dd), 3.19(dd), 3.12(m), 2.05–1.5(m), 1.4(m), 1.31(d).

EXAMPLE 18

(4S,8S,9R,10S,12R)-4-amino-10-(1-hydroxyethyl)11-oxo-1-azatricyclo[7.2.0.0$^{3,8}$]undec-2-ene-2-carboxylic acid A solution of the Example 17 (0.4 g) and acetic acid (0.24 g) in dry tetrahydrofuran (10 ml) was stirred under nitrogen for 15 min. Tetrakis (triphenylphosphine) palladium (0.650 g), dissolved in dry tetrahydrofuran (15 ml), was then added and the mixture stirred for 1 hr. The obtained solid was filtered off, washed with diethylether and dried, to give the title compound as a pale yellow solid (0.230 g); IR: V$_{max}$ (Nujol) 3364–2669, 1767, 1872, cm$^1$; $^1$-NMR (300 MHZ, D$_2$O-Acetone) 5.0(m), 4.12–4.0(m), 3.32(m), 3.09(m), 2.0–1.5(m), 1.25(m), 1.12(d).

EXAMPLE 19

Ally-(4S,8S,9R,10S,12R)-4-allyloxycarbonylaminomethyl)-10-[1-(t-Butyldimethylsilyloxy)-ethyl]-11-oxo-1-azatricylco-[7.2.0.0$^{3,8}$]undec-2-ene-2-carboxylate Intermediate 20 (0.48 g) was dissolved in dry methylene chloride (20 ml) at room temperature, potassium carbonate (1 g) was added followed by allyloxallylchloride (0.18 ml) and triethylamine (0.18 ml). After 5 hr the mixture was filtered, diluted with methylene chloride (80 ml), washed with a 5% of sodium hydrogen carbonate solution and brine (30 ml). The organic layer was dried and evaporated under reduced pressure. The residue which was dissolved with dry xylene (100 ml) triethylphosphite (0.8 ml) and hydroquinone (0.05 g) were added and the mixture was refluxed for 3.5 hr.

The solvent was evaporated under reduced pressure to give an oil which was purified by flash chromatography on silica gel (eulants ether and cyclohexane 80/20 Rf=0.7) to afford the title compound (0.30 g) as a yellow oil.

IR (cm$^{-1}$): 3450(NH), 1769(*CO), 1744(CO), 1715(CO);

NMR(ppm)5.92(m), 5.5–5.1(m), 4.9(m), 4.8–4.5(m), 4.18(m), 4.11(dd), 3.72(m), 3.55(m), 3.3–3.0(m), 2.0–1.2(m), 1.36(t), 1.19(d), 0.86(s), 0.05(s).

EXAMPLE 20

Allyl(4S,8S,9R,10S,12R)-4-(allyloxycarbonylaminomethyl)-10-(1-hydroxyethyl)-11-oxo-1-azatricylco[7.2.0.0$^{3,8}$]-undec-2-ene-2-carboxylate Example 19 (0.30 g) was dissolved in dry tetrahydrofuran, acetic acid (0.3 ml) and tetrabutylammonium fluoride (2.5 ml of M solution in THF) were added and the mixture was stirred for 30 hours. The mixture was diluted with ethyl acetate (150 ml) and washed twice with brine (100 ml) and with a 5% aq. sodium hydrogen carbonate solution (80 ml). The organic layer was dried and evaporated under reduced pressure to give a residue which was purified by flash chromatography on silica gel (eulants cyclohexane and ethyl acetate 50/50 Rf=0.1) to afford the title compound (0.06 g) as a colourless oil.

IR (V$_{max}$ cm$^{-1}$): 3605(OH), 3447(NH), 1771(CO), 1717(CO), 1620 (C=C);

NMR (CDCl—$_3$ ppm): 6.0–5.8(m), 5.5–51(m), 4.93(bm), 4.8–4.6(m), 4.48(m), 4.3–4.1(m), 3.73(m), 3.58(m), 3.3–3,.1(m), 1.75–1.2(m), 1.27(d).

EXAMPLE 21

(4S,8S,9R,10S,12R)-4-(aminomethyl)-10-(1-hydroxyethyl)-11-oxo-1-azatricylco[7.2.0.0$^{3,8}$]- undec-2-ene-2-carboxylic acid Example 20 (0.06 g) was dissolved in dry tetrahydrofuran (1 ml), acetic acid (0.036 ml), and tetrakis(triphenylphospine)palladium (0.09 g) were added. The mixture kept under stirring for 1 hour was diluted with a mixture of ether (8 ml) and petroleum ether (4 ml). The obtained solid was washed twice with a mixture of ether (8 ml) and petroleum ether (4 ml). The solid was dissolved in water (5 ml) and chromatographed on reverse phase silica gel C-18(eulant water) and the solution was freeze dried to give the title compound (0.04 g) as a white solid.

IR (Nujol, cm$^{-1}$):3300–2650(NH3+,OH,NH2), 1751(CO) 1582(C=C,CO)

NMR (D20 ppm): 7.62(m), 4.78(m), 4.07(m), 4.00(dd), 3.9–3.65(m), 3.24(m), 3.3–2.9(m), 2.1–1.95(m), 1.8–1.4(m), 1.3–1.0(m), 1.11(d), 1.02(d), UV (V$_{max}$ nm): 268.5.

EXAMPLE 22

(a) Allyl-(4S,8S,9R,10S,12R)-4-isopropoxy-10-[1-(t-butyldimethylsilyloxy) ethyl]-11-oxo-1-azatricylco-[7.2.0.0$^{3,8}$]-undec-2-ene-2-carboxylate To an ice-cold solution of intermediate 23a (1.13 g) in anhydrous dichloromethane (150 ml), solid K$_2$CO$_3$ was added. The mixture was stirred for 30' under nitrogen, then allyloxalylchloride (4.43 ml) followed by triethylamine (5 ml) in several portions was added during 40 hrs at 25° C. until complete conversion of the starting material. After filtration the organic layer was washed with brine, dried, and evaporated under reduced pressure. The oily residue (1.05 g), corresponding to the crude oxalimide intermediate, was dissolved in dry (40 ml) xylene and triethylphosphite (1.445 ml) was added and the mixture was heated with stirring at 140° C. for 3 hrs. The reaction mixture was then cooled, evaporated under reduced pressure and chromatographed, using a mixture cyclohexane/ethyl acetate 1/1 as eluant, to obtain the title compound as an yellow oil (0.33 g; t.l.c. cyclohexane/ethyl acetate 1/1 Rf 0.68); IR (CDCl$_3$) V$_{max}$ (cm$^{-1}$): 1772(C=O β-lactam), 1717(C=O allyl ester)

H$^1$-NMR(CDCl$_3$): 6(m), 5.43(m), 5.26(m), 5.18(m), 4.86–4.6(m), 4.21(m), 4.125(dd), 3.55(m), 3.18(dd), 3.20(m), 2.05–1.5(m), 1.5–1.2(m), 1.23(d), 1.14(dd), 0.88(s) ppm.

(b) In a similar manner Allyl(4R,8S,9R,10S,12R)-4-Isopropoxy-10-[1-(t-Butyldimethylsilyloxy)-ethyl]-11-oxo-1-azatricylco[7.2.0.0$^{3,8}$]- undec-2-ene-2-carboxylate (0.2 g t.l.c. cyclohexane/ethyl acetate 7/3 Rf 0.67); IR(CDCl$_3$), V$_{max}$ cm$^{-1}$): 1765(C=O β-lactam), 1744(C=O allyl ester), 1612(C=C) H$^1$-NMR (CDCl$_3$): 5.94(m), 5.33(m), 4.73(m), 4.17(dd), 3.67(m), 3.23(dd), 2.78(m), 2.4–1.2(m), 1.22(d), 1.10(m), 0.88(s), 0.018(s)ppm., was obtained from intermediate 23b (1.64 g) except that the chromatrography elutant was a 7/3 mixture of cyclohexane/ethyl acetate.

EXAMPLE 23

(a) Allyl(4S,8S,9R,10S,12R)-4-isopropoxy-10-(1-hydroxyethyl)-11-oxo-1-azatricylco[7.2.0.0$^{3,8}$]- undec-2-ene-2-carboxylate The Example 22a (0.330 g) was dissolved in tetrahydrofuran (30 ml) and acetic acid (0.325 ml) was added followed by tetrabutylammonium fluoride trihydrate (0.674 g). The mixture was stirred at 20° C. for 20 hrs, then diluted with ethyl acetate (50 ml) and washed with a 2% solution of sodium hydrogen carbonate and brine (50 ml). After evaporation, the residue was purified by flash chromatography, using a mixture, cyclohexane/ethyl acetate 1/1 as eluant, to obtain the title compound as an oil (0.12 g; t.l.c. cyclohexane/ethyl acetate 1/1 Rf 0.15); IR:V$_{max}$ Cm$^{-1}$ 3614(OH); 1772(C=Oβ-lactam) 1717(C=Oester) 1632(C=C); H$^1$-NMR(CDCl$_3$) (CDCl$_3$): 5.96(m), 5.45(m), 5.27(m), 5.18(m), 4.82(m), 4.69(m), 4.25(m), 4.18(dd), 3.53(m), 3.3(m), 3.23(dd), 2.0(m), 1.88(m), 1.77(m), 1.7–1.2(m), 1.33(d), 1.13(dd) ppm.

(b). Allyl(4R,8S,9R,10S,12R)-4-isopropoxy-10-(1-hydroxyethyl)-11-oxo-1-azatricylco[7.2.0.0$^{3,8}$]- undec-2-ene-2-carboxylate The Example 22b (0.2 g) was dissolved in tetrahydrofuran (50 ml) and acetic acid (0.197 ml) was added followed by tetrabutylammonium fluoride trihydrate (0.408 g). The mixture was stirred at 20° C. for 24 hrs. Then brine (50 ml) was added and the mixture was extracted with ethyl acetate (3×20 ml). The organic layer was extracted with a solution of sodium hydrogen carbonate (2×25 ml), then with brine (brine). After concentration, the residue was purified by flash chromatography, using a mixture cyclohexane/ethyl acetate 7/3 as eluant, to obtain the title compound as an oil (0.04 g t.l.c. cyclohexane/ethyl acetate 1/1 Rf 0.13); IR (CDCl$_3$), V$_{max}$ (cm$^{-1}$) 1776(C=O β-lactam); 1720(C=O allyl ester), 1609(C=C), 3600(OH) H$^1$-NMR (CDCl$_3$): 5.93(m), 5.40(m), 4.70(m), 4.20(dd), 4.19(m), 4.05(m), 3.66(m), 3.26(dd), 2.81(m), 2.1–1.2(m), 1.29(d), 1.08(m) ppm.

EXAMPLE 24

(a) Potassium(4S,8S,9R,10S,12R)-4-isopropoxy-10-(1-hydroxyethyl)-11-oxo-1-azatricylco[7.2.0.0$^{3,8}$]-undec-2-ene-2-carboxylate The Example 23a (0.12 g) was dissolved in anhydrous dichloromethane (20 ml) and triphenylphosphine (0.09 g), followed palladium tetrakis (triphenylphosphine) (0.13 g ) and a 0.5M solution of potassium 2-ethylhexanoate (0.568 ml) were added. The crude solid (22 mg), obtained by filtration, was purified by reverse phase chromatography (R$_p$18; water as eluant). Fractions containing the product were combined and freeze dried. The title compound was obtained as a white solid (10 mg); IR Nujol, V$_{max}$ (cm$^{-1}$); 3375(OH), 1731(C=O β-lactam), 1593(bb C=C and C=O carboxylate)

H$^1$-NMR (H$_2$O/acetone): 4.99(m), 4.08(m), 4.0(m), 3.49(m), 3.26(m), 3.05(m), 1.8–1.2(m), 1.11(d), 0.98(m), ppm.

(b) Potassium(4R,8S,9R,10S,12R)-4-isopropoxy-10-(1-hydroxyethyl)-11-oxo-1-azatricylco[7.2.0.0$^{3,8}$] undec-2-ene-2-carboxylate The Example 23b (0.03 g) was dissolved in anhydrous dichloromethane (10 ml). Then triphenylphosphine (0.0022 g) was added, followed by palladium tetrakis(-triphenylphospine) (0.0033 g) and 0.05M solution of potassium 2-ethylhexanoate (0.16 ml). The reaction mixture was stirred for two hrs under nitrogen, then the solvent was evaporated to small volume and the resulting mixture was diluted with diethyl ether (5 ml). The solid obtained was filtered, washed with diethyl ether/petroleum ether and dried to give the title compound as a white solid (0.022 g);

IR (CDCl$_3$), V$_{max}$ (cm$^{-1}$): 1751 (C=O β-lactam), 1595 (C=O,C=C)

H$^1$-NMR D$_2$O: 4.02(m), 4.1–4(m), 3.6(q), 3.24(dd), 2.67(m), 2.05(m), 1.79(m), 1.6(m), 1.1(d), 0.9(s), 1.4(m) ppm.

EXAMPLE 25

Allyl(4S,8S,9R,10S,12R)-4-cyclopentyloxy-10-[1-(t-Butyldimethylsilyloxy)-ethyl]-11-oxo-1-azatricylco[7.2.0.0$^{3,8}$]-undec-2-ene-2-carboxylate To an ice cold solution of the intermediate 25 (1.2 g) in anhydrous dichloromethane (60 ml), solid K$_2$CO$_3$ (300 mg) and 4A molecular sieves were added. To the stirred solution, allyl oxalylchloride (0.48 mg) and triethylamine (0.33 mg) were added and the resulting mixture was stirred at 20°, under nitrogen for 3 hr. The solid was filtered off and the solution washed with 10% NaHCO$_3$ solution, brine, dried over sodium sulfate and evaporated under reduced pressure. The crude oxalimide intermediate was dissolved in dry xylene (50 ml) and triethylphosphite (4.6 ml) was added. The resulting solution was heated under stirring at 80° for 1 hr, then at 140° for 3 hrs. The reaction mixture was cooled and evaporated under reduced pressure. The residue was chromatographed on silica gel using cyclohexane as eluant to give the title compound as a yellows oil (0.75 g t.l.c. cyclohexane/ethyl acetate 1/1 Rf 0.6) IR (CDCl$_3$), $v_{max}$(cm$^{-1}$): 1771 (C=O $\beta$ lactam), 1738 (C=O), 1601 (C=C). H-$^1$-NMR (CDCl$_3$): 5.38(m), 5.23(m), 4.70(m), 4.11(m), 3.99(m), 3.74(dd), 3.09(dd), 2.89(m), 2.10(m), 1.90(m), 1.80–1.20(m), 1.23(d), 0.86(s), 0.05(s).

EXAMPLE 26

Allyl(4S,8S,10S,12R)-4-cyclopentyloxy-10-(1-hydroxyethyl)-11-oxo-1-azatricylco[7.2.0.0$^{3,8}$]-undec-2-ene-2-carboxylate To the stirred solution of Example 25 in dry THF (40 ml), acetic acid (0.75 mg) and tetrabutylammonium trihydrate (1.80 g) were added. The mixture was stirred at 20° for 24 hrs then poured into water and extracted with ethyl acetate; the organic layer was washed with 10% solution of NaHCO$_3$, brine dried over MgSO$_4$ and evaporated under reduced pressure. The residue was purified by flash chromatography, using a mixture of cyclohexane/ethyl acetate 8/2 as eluant, to obtaine the title compound 4b as an oil. (0.19 g; t.l.c. cyclohexane/ethyl acetate 3/7 Rf 0.3). IR (CDCl$_3$), $V_{max}$ (cm$^{-1}$): 3600(Oh), 1776 (C=O $\beta$ lactam), 1738 (C=O) 1603 (C=C).

H$^1$-NMR (CDCl$_3$): 5.95(m), 5.39(m), 5.26(m), 4.71(m), 4.16(m), 4.09(m), 4.00(m), 3.79(dd), 3.18(dd), 2.90(m), 2.10(m), 1.90(m), 1.8–1.2(m), 1.31(d).

EXAMPLE 27

Potassium(4S,8S,9R,10S,12R)-4-cyclopentyloxy-10-(1-hydroxyethyl)-11-oxo-1-azabicyclo[7.2.0.0$^{3,8}$]-undec-2-ene-2-carboxylate To the stirred solution of Example 26 (0.17 g) in dry ethyl ethyl acetate (9 ml) and dry methylene chloride (9 ml), triphenyl phosphine (18 mg), tetrakis (triphenylphosphine) palladium (23.6 mg) and 0.5M solution of potassium ethyl exanoate (0.85 ml) were added. The mixture was stirred under nitrogen at 20 C. for 4 hr. A 1/1 solution of diethyl ether/petroleum (15 ml) was then added, the obtained solid was filtered off, washed with 1/1 diethyl ether/petroleum solution (3×15 ml), and dried to give the title compound (0.10 g; t.l.c. methylene chloride/acetic acid 9/1 Rf 0.2 IR (Nujol), V$_{max}$ (cm$^{-1}$): 1772–1680(C=O); 1640, 1585 (C=C).

H$^1$-NMR (D$_2$O): 4.05(m), 3.89(m), 3.62(dd), 3.22(dd), 2.83(m), 1.9–1.0(m), 1.11(d).

EXAMPLE 28

Allyl-(4S,8S,9R,10S,12R)-4-(t-Butyldimethylsilyloxymethyl)-10[1-(t-Butyldimethysilyloxy)-ethyl]-11-oxo-1-azatricyclo[7.2.0.0$^{3,8}$]-undec-2-ene-2-carboxylate Intermediate 27 (5.2 g) were dissolved in anhydrous methylene chloride (100 ml) and anhydrous potassium carbonate (1 g) was added. Allyloxalylchloride (1.9 ml) and triethylamine (1.9 ml) were added to the stirred solution at room temperature, and the resulting mixture was stirred for 2.5 hours filtered and washed twice with a saturated aqueous solution of sodium hydrogen carbonate (80 ml). The organic layer was dried and the oil obtained after evaporation was partially purified from polar impurities by flash chromatography (eluants cyclohexane/ethyl acetate 98/2 Rf=0.7). The eluants were removed by evaporation and the residue dissolved in dry xylene (150 ml) and triethylphosphite (8.3 ml) was added. The solution was refluxed for 4 hours and the solvent removed under reduced pressure. The oily residue was chromatographed on silica (eluants cyclohexane/ethyl acetate 98/2 Rf=0.7) to afford the title compound (1.8 g) as a yellow oil.

IR: (V$_{max}$ cm$^{-1}$) 1769, 1715 and 1647;

NMR: (d ppm) 5.96(m), 5.33(m), 4.72(m), 4.18(m), 4.18(m), 4.07(dd), 3.75(m), 3.16(dd), 3.0(m), 1.95(m), 1.9–1.7(m), 1.3(m), 1.23(m), 0.87(s), 0.07(s), 0.03(s).

EXAMPLE 29

Allyl-(4S,8S,9R,10S,12R)-4-(hydroxymethyl)-10-(1-hydroxyethyl)-11-oxo-1-azatricylco[7.2.0.0$^{3,8}$]undec-2-ene-2-carboxylate To a stirred solution of Example 28 (90 mg) dissolved in anhydrous THF (15 ml), acetic acid (0.1 ml) and tetrabutylammonium fluoride (0.82 ml of 1M solution in THF) were added. The resulting mixture was stirred for 30 hours then diluted with ethyl acetate (100 ml) and washed with 2% aq. sodium hydrogen bicarbonate, ice water and brine. The organic layer was dried and evaporated under reduced pressure to give an oil which was chromatographed on silica gel (eluants cyclohexane/ethyl acetate 50/50 Rf=0.2) to afford the title compound a colourless oil (25 mg).

IR: (V$_{max}$ cm$^{-1}$) 3605, 3497, 1771, 1713 and 1620;

NMR: (d ppm), 5.98(m), 5.35(m), 4.74(m), 4.23–4.18(m+dd), 3.78(m), 3.24(dd), 3.08(m), 2.1–1.2(m), 1.31(d).

EXAMPLE 30

Potassium(4S,8S,9R,10S,12R)-4-(hydroxymethyl)-10-(1-hydroxyethyl)-11-oxo-1-azatricylco[7.2.0.0$^{3,8}$]-undec-2-ene-2-carboxylate Example 29 (25 mg) was dissolved in anhydrous THF (1.5 ml), tetrakis(triphenylphosphine)palladium (10 mg), triphenylphosphine (10 mg) and potassium 2-ethylhexanote (0.14 ml of 0.5M in ethyl acetate) were dissolved in 0.5 ml of anhydrous THF and added to the solution, the mixture was stirred for an hour then diluted with dry ether (15 ml) and petroleum ether (10 ml). The solid was washed twice with dry ether (15 ml) and petroleum ether (10 ml). The solid was dissolved in water (0.2 ml) and chromatographed on reverse phase silica gel C-18 (eluant water), the solution was freeze dried to give the title compound (10 mg.) as a while solid.

IR: (Nujol, cm$^{-1}$) 1751 and 1583;

NMR (d ppm, D$_2$O) 4.06(m), 3.57(m), 3.178(dd), 3.51(m), 2.92(m), 1.50(m).

EXAMPLE 31

Allyl(4S,8S,9R,10S,12R)-4-(1)-phenylthio-10-[1-(t-Butyldimethylsilyloxy)ethyl]-11-oxo-1-azatricylco[7.2.0.0$^{3,8}$]-undec-2-ene-2-carboxylate To a solution of intermediate 29a (0.75 g) in anhydrous methylene chloride (25 ml), anhydrous potassium carbonate (0.24 g) was added and the mixture was stirred at 23 C. for 15 min. The mixture was cooled at 0° C. and allyl oxalyl chloride (0.385 g) was added by a syringe followed by triethylamine (0.36 ml). The reaction was stirred at 23 C. for 0.5 hrs, the solid was filtered off washing with methylene chloride (20 ml). The solvent was evaporated and to the resulting mixture ethyl ether (40 ml) and brine (20 ml) were added. The two layers were extracted and separated, the organic phase was extracted with brine (20 ml) 5% sodium hydrogen carbonate (6×20 ml) water (20 ml) a cold 1% solution of hydrochloric acide (3×20 ml) and water (20 ml). The organic layer gave, after evaporation a yellow oil (0.85 g) which was dissolved in anhydrous xylene, triethyl phosphite (2.87 g) was added and the resulting solution was heated under stirring for 16 hrs. the reaction was evaporated and the oily residue was submitted to flash chromatography (CH/EA 8/2). The title compound (0.29 g, 32.6%) was obtained Rf=0.7, CH/EA 7/3) as a white wax.

IR (cm$^{-1}$) 1774 ($\beta$-lactam); 1717(carboxyl); 1651(double bond); 1626(double bond); 1583(double bond).

$^1$H-NMR (ppm) 7.37(m); 7.20(m), 5.81(m); 5.25(m); 5.17(m); 4.54(m), 4.13(m), 4.06(dd); 3.39(m); 3.14(dd); 2.04(m); 2.0–1.8(m); 1.8–1.65(m); 1.37(m); 1.19(d); 0.85(s).

EXAMPLE 32

Allyl(4S,8S,9R,10S,12R)-4-phenylthio-10-(1-hydroxyethyl)-11-oxo-1-azatricyclo[7.2.0.0$^{3,8}$]-undec-2-ene-2-carboxylate To a stirred solution of Example 31 (0.13 g) in anhydrous THF under nitrogen, acetic acid was added by a syringe: (0.116 ml) followed by a solution of tetrabutylammonium fluoride trihydrate (0.239 g) in THF (6 ml). The resulting mixture was stirred for 20 hrs and diluted with brine (10 ml), extracted 3 times with ethyl acetate (30 ml). The organic layer was washed twice with a 5% solution of sodium hydrogen carbonate (30 ml) and with brine (30 ml). The residue, after evaporation, was purified by flash chromatography (CH/EA gradient elution from 7/3 to 1/1) to obtain 5 (0.08 g) eluted first and the title compound (0.03 g, 30%) eluted second as a colourless oil (Rf=)0.3, CH/EA 1/1)

IR(cm$^{-1}$) 3612(hydroxyl); 1772 ($\beta$-lactam); 1717(carboxy); 1649 (double bond); 1626(double bond); 1583(double bond).

$^1$H-NMR (ppm) 7.38(m); 7.26(m); 5.83(m); 5.22(sa); 4.58(m); 4.20(m); 4.15(dd); 3.51(m); 3.22(dd); 2.2–1.5(m); 1.4(m); 1.3(d).

EXAMPLE 33

Potassium(4S,8S,9R,10S,12R)-4-(1-phenylthio-10-((1-hydroxy)ethyl)-11-oxo-1-azatricyclo[7.2.0.0$^{3,8}$]-undec-2-ene-2-carboxylate To a solution of Example 32 (30 mg) in a 1/1 mixture of methylene chloride and ethyl acetate (2 ml), under nitrogen a solution of triphenyl phosphine (2 mg) in methylene chloride (0.5 ml) was added followed by a solution of palladium tetrakis(triphenylphosphine) in methylene chloride (0.5 ml) and by a 0.5M solution of potassium 2-ethylhexanoate in ethyl acetate (0.125 ml). The solution was stirred for 1 hr. The precipitate which formed was separated after centrifugation, washed three times with ethyl ether to yield the title compound as a white solid (6 mg, 20.).

IR(Nujol, cm$^{-1}$) 3344(hydroxyl); 1765 ($\beta$-lactam); 1645(double bond); 1591(double bond).

$^1$H-NMR (D$_2$O pm) 7.20(m), 5.17(bs); 4.01(m); 3.87(dd); 3.18(m+dd); 1.9–1.5(m), 1.25(m); 1.08(d).

EXAMPLE 34

Allyl(4S,8S,9R,10S,12R)-4-(N-allyloxycarbonyl-N-methylamino)-10-[1-(t-butyldimethylsilyloxy)-ethyl]-11-oxo-1-azatricyclo[7.2.0.0$^{3,8}$]-undec-2-ene-2-carboxylate A solution of the intermediate 35 in anhydrous xylene (120 ml) was stirred in presence of 4A molecular sieves, at 22° under nitrogen for 1 hr, then triethylphosphite (25 ml) was added and the solution heated at reflux for 7 hrs, then the solvent was removed under vacuum. The residue was chromatographed on silica gel, using a mixture of diethylether/petroleum (7/3) as eluant, to afford the title compound as a yellow oil (3 g, t.l.c. diethyl ether Rf 0.76); IR; V$_{max}$ (CDCl$_3$) 1767, 1744, 1693, 1649 cm$^{-1}$; $^1$H-MNR (300 MHZ, CDCl$_3$) 5.96(m), 5.5–5.1(m), 5.36(m), 4.8–4.5(m), 4.21(m), 4.16(dd), 3.20(m), 3.0(s), 2.25–2.1(m), 1.92–1.8(m), 1.75–1.4(m), 1.38(t), 1.23(d), 0.88(s), 0.078(s), 0.075(s).

EXAMPLE 35

Allyl-(4S,8S,9R,10S,12R)-4-(N-allyloxycarbonyl-N-methylamino)-10-(1'-hydroxyethyl)-11-oxo-1-azatricyclo[7.2.0.0$^{3,8}$]-undec-2-ene-2-carboxylate To a solution of Example 34 (3.0 g) in dry tetrahydrofuran (50 ml), acetic acid (2.6 ml) and a solution of tetrabutylammonium fluoride trihydrate (5.5 g) in dry tetrahydrofuran (30 ml) were added. The mixture was stirred at 22° for 15 hrs, then poured into water (200 ml) and extracted with ethyl acetate (2×80 ml). The organic layer was washed with 5% sodium hydrogen carbonate solution (2×80 ml) and brine (100 ml), dried over anhydrous sodium sulfate and evaporated under vacuum. The residue was chromatographed on silica gel, using a mixture of methylene chloride/methanol (9/1) as eluant, to give the title compound as a colourless oil (0.77 g); IR: V$_{max}$ (CDCl$_3$) 3612, 1776, 1720, 1713 1700 cm$^{-1}$; $^1$H-MNR (300 MHZ, CDCl$_3$) 5.94(m), 5.5–5.15(m), 5.35(t), 4.73(m), 4.56(m), 4.23(m), 4.21(dd), 3.24(dd), 3.23(m), 2.99(s), 2.20(m), 1.91(m), 1.8–1.5(m), 1.4(m), 1.32(d).

EXAMPLE 36

(4S,8S,9R,10S,12R)-4-methylamino-10-(1-hydroxyethyl)-11-oxo-1-azatricyclo[7.2.0.0$^{3,8}$]-undec-2-ene-2-carboxylic acid To a solution of Example 35 (1.2 g) in dry tetrahydrofuran (50 ml) dimedone (1.67 g) was added under nitrogen at 22°. The solution was stirred for 15 min, then a solution of tetrakis(triphenylphosphine) palladium (1.7 g) in dry tetrahydrofuran (70 ml) was added dropise in 10 min and the mixture stirred for 1 hr. Diethyl ether (200 ml) was added dropwise in 5 min under stirring and the resulting solid was filtered off, washed with diethylether (3×15 ml) and dried. Then the solid was dissolved in water (19 ml) washed with ethyl acetate (5×15 ml) and ice dried to give the title compound a pale yellow solid (0.6 g); IR: V$_{max}$ (Nujol) 3370–1700, 1767, 1597, cm$^{-1}$; $^1$H-NMR (300 MHZ, D$_2$O-Acetone) 4.81(m), 4.15–4.02(m), 3.36(dd), 3.03(m), 2.47(s), 2.01–1.9(m), 1.33(m), 1.10(d).

EXAMPLE 37

Allyl-(4S,8S,9R,10S,12R)-4-(2-allyloxycarbonylaminoethoxy)-10-[1-(t-butyldimethylsilyloxy)-ethyl-11-oxo-1-azatricyclo[7.2.0.0$^{3,8}$]-undec-2-ene-2-carboxylate To a solution of the intermediate 40 in anhydrous dichloromethane (40 ml), solid potassium carbonate (0.5 g), then allyl oxalyl chloride (0.4 ml) and triethylamine (0.4 ml) were added at room temperature. After 3 hr. the mixture was diluted with dichloromethane (100 ml), filtered and washed with cold 5% solution of sodium hydrogen carbonate (2×40 ml). The organic layer was dried and evaporated. The residue was dissolved in anhydrous xylene (100 ml, hydroquinone (0.02 g), triethylphosphite (1.6 ml) were added and the mixture was heated at 110° C. for 3 hr, then the solvent was removed under vacuum. The residue was chromatographed on silica gel using a ethyl acetate/cyclohexane 3/7 mixture as eluant to afford the title compound (0.52 g t.l.c.; ethyl acetate/cyclohexane 1/1 Rf=0.8).

IR (CDCl$_3$ V$_{max}$ (cm$^{-1}$)3454(N-H), 1774(lactam), 1718(C=O), 1651(C=O), H$^1$-NMR (CDCl$_3$): 6.20–5.85(2 m). 5.48–0.10(2 m), 5.085(m). 5.04(bs), 4.82–4.64(m), 4.58(d), 4.216(m), 4.15(dd), 3.50–3.30(m), 3.195(dd), 3.15(m), 0.05(m), 1.88–1.55(m), 1.52–1.20(m), 1.22(d), 0.0887(s), 0.082(s), 0.077(s).

EXAMPLE 38

Allyl-(4S,8S,9R,10S,12R)-4-(2-allyloxycarbonylaminoethoxy)-10-[1-hydroxyethyl)-11-oxo-1-azatricyclo[7.2.0.0$^{3,8}$]-undec-2-ene-2-carboxylate To a solution of the Example 37 (0.52 g) in dry tetrahydrofuran (50 ml), acetic acid (0.4 ml) and a 1M solution of tetrabutyl ammonium fluoride (5.5 ml) in dry tetrahydrofuran were added. The mixture was stirred for 36 hr. at room temperature, diluted with ethyl acetate (100 ml) and washed with a saturated ammonium chloride solution (1×40 ml) and a 5% sodium hydrogen carbonate solution (2×40 ml). The organic layer was dried evaporated and chromatographed on silica gel using a ethyl acetate/cyclohexane 6/4 mixture as eluant to afford the title compound (0.2 g, t.l.c.; ethyl acetate/cyclohexane 6/4 Rf=0.1).

IR (CDCl$_3$ V$_{max}$ (cm$^{-1}$) 3609 and 3499 (N—H, OH), 1722 (lactam), 1718(C=O)

H$^1$-NMR (CDCl$_3$): 6.02–5.84(m), 5.5–5.18(m), 5.08(t), 5.02(sa), 4.88–4.64(m), 4.57(m), 4.24(m), 4.18(m), 3.44–3.3(m), 3.28–3.14(m), 2.05(m), 1.92–1.25(m), 1.32(d)

EXAMPLE 39

(4S,8S,9R,10S,12R)-4-(2-aminoethoxy)-10-[1-hydroxyethyl)-11-oxo-1-azatricyclo[7.2.0.0$^{3,8}$]-undec-2-ene-2-carboxylic acid To the solution of the Example 38 (0.04 g) in dry tetrahydrofuran (2 ml), acetic acid (0.05 ml) and tetrakis (triphenylphosphine) palladium (0.05 g) in tetrahydrofuran (0.5 ml) were added. After 4 hr. diethyl ether (10 ml) and petroleum ether (5 ml) were added and the resulting solid was centrifuged, washed with diethyl ether (3×10 ml) and dried. The solid was purified on C-18 (cartridge SEP-PAK Water Associates) using water as eluant, then the sample dissolved in water and freeze dried to afford the title compound (1 mg) as a white solid.

IR (CDCl$_3$ V$_{max}$ (cm$^{-1}$)3358–3100(NH$_2$), 1763 (lactam), 1595(C=O, C=C).

H$^1$-NMR (D$_2$O): 4.91(m), 4.08(m), 4.04(dd), 3.58–3.40(m), 3.28(dd), 3.12–2.93(m), 1.9(m), 1.80–1.30(m), 1.25(m), 1.11(d).

EXAMPLE 40

Benzyl 4-methoxy-10-(1-hydroxyethyl)-11-oxo-1-azatricyclo[7.2.0.0$^{3,8}$]-undec-2-ene-2-carboxylate To a solution of the intermediate 41 (0.54 g) in dry tetrahydrofuran (5 ml) under nitrogen at 0° thionyl chloride (0.15 ml) and 2,6lutidine (0.27 ml) were added. The reaction mixture was stirred at 22° for 3 hrs., diluted with ethyl acetate (2 ml) and washed with saturated aq. ammonium chloride (2×25 ml), 5% aq. sodium hydrogen carbonate (2×25 ml) brine (2×25 ml), dried and evaporated in vacuo. The oily residue (0.56 g) was dissolved in 1,4-dioxane (10 ml) and 2,6-lutidine (0.18 ml), sodium bromide (0.21 g) and triphenylphosphine (0.54 g) were added. The reaction mixture was stirred at 22° for 15 hrs. then heated at reflux for 2 hrs. The reaction mixture was diluted with ethyl acetate (50 ml) and washed with saturated aq. ammonium chloride (2×50 ml) and brine (2×50 ml), dried and concentrated under vacuum. The oily residue was chromatographed on silica gel, using a mixture of petroleum ether/diethyl ether 9/1 as eluant, to afford a colourless oil (0.16 g). This was dissolved in dry tetrahydrofuran (5 ml), acetic acid (0.14 ml) and a 1.1M solution of N,N,N-tetrabutylammonium fluoride in dry tetrahydrofuran (084 ml) were added. The reaction mixture was stirred at 22° for 15 hrs. diluted with ethyl acetate (25 ml) and washed with 5% aq. sodium hydrogen carbonate (3×25 ml) brine (2×25 ml), dried and concentrated under vacuum. The residue was chromatographed on silica gel, using a mixute of ethyl acetate/cyclohexane 3/7 as eluant, to give the title compound as a colourless oil (35 mg; t.l.c. cyclohexane/ethyl acetate 1/1; Rf=0.3). IR (CDCl$_3$ V$_{max}$ (cm$^{-1}$) 3600(O-H), 1772(C=O β lactam), 1718(C=O ester), 1632(C=C); H$^1$-NMR (300 MHzCDCl$_3$): 7.47–7.30(m), 5.29(dd), 4.94(t), 4.24(m), 4.19(dd), 3.3=3.3.2(m), 3.20(s), 2.05(m), 1.9–1.2(m), 1.61(d), 1.32(d).

EXAMPLE 41

Potassium (4S,8S,9R,10S,12R)-4-methoxy-10-(1-hydroxethyl)-11-oxo-1-azatricyclo[7.2.0.0$^{3,8}$]-undec-2-ene-2-carboxylate To a solution of the Example 40 (30 mg) in ethyl acetate (1 ml), ethyl alcohol (1 ml) and palladium black (11 mg) were added and the mixture was stirred in a hydrogen atmosphere (1 atm) at 25° for 25 min. Then the catalyst was filtered off and the solution was extracted with 0.4% potassium hydrogen carbonate (2.5 ml). The aqueous layer was concentrated under vacuum, then purified by reverse phase chromatography. The aqueous solution was freeze dried to give the title compound as a white solid (20 mg).

EXAMPLE 42

Benzyl 4-methoxy-10-[(1-hydroxyethyl-11-oxo-1-azatricyclo[7.2.0.0$^{3,8}$]-undec-2-ene-2-carboxylate To a solution of the intermediate 41 (1 g) in dry tetrahydrofuran (10 ml) under nitrogen at 0°, thionyl chloride (0.27 ml) and 2,6-lutidine (0.48 ml) were added. The reaction mixture was stirred at 22° for 3 hrs, diluted with ethyl acetate (50 ml) and washed with saturated aq. ammonium chloride (2×50 ml), 5% aq. sodium hydrogen carbonate (2×50 ml), brine (2×50 ml), dried and concentrated under vacuum. The oily residue (1.1 g) was dissolved in 1,4-dioxane (20 ml) and 2,6-lutidine (0.33 ml), sodium bromide (0.39 g), triphenylphosphine (0.98 g) were added. The reaction mixture was stirred at 22° for 15 hrs, then poured into saturated aq. ammonium chloride (50 ml) and extracted with ethyl acetate (50 ml). The organic layer was washed with saturated aq. ammonium chloride (50 ml) and brine (2×50 ml), dried and concentrated under reduced pressure. The oily residue was chromatographed on silica gel, using a mixture of ethyl acetate/cyclohexane 3/7 as eluant, to give an oil (1.0 g t.l.c. ethyl acetate/cyclohexane 1/1 Rf=0.6). The oil was dissolved in acetonitrile (15 ml), and acetic acid (1.3 ml) and conc. hydrocloric acid (1 ml) were added at ice cooling. The reaction mixture was stirred at 0° for 1 hr, then poured into cold 5% aq. sodium hydrogen carbonate (50 ml) and extracted with ethyl acetate (50 ml). The organic layer was washed with brine, dried, and concentrated under reduced pressure to give a white foam (0.9 g t.l.c. ethyl acetate/cyclohexane; 25/5 Rf=0.36). This was dissolved in 1,4-dioxane (20 ml), heated at reflux for 5 hrs, and then the solvent was removed under vacuum. The oily residue was chromatographed on silica gel, using a mixture of ethyl acetate/cyclohexane 1/1 as eluant, to afford the title compound as a colourless oil (0.26 g; t.l.c. ethyl acetate/cyclohexane 1/1 Rf=0.3).

EXAMPLE 43

Sodium (4S,8S,9R,10S,12R)-4-methoxy-10-(1-hydroxyethyl)-11-oxo-1-azatricyclo[7.2.0.0$^{3,8}$]undec-2-ene-2-carboxylate To a solution of Example 42 (0.195 g) in ethyl acetate (8 ml), ethyl alcohol (8 ml) and palladium black (75.3 mg) were added. The reaction mixture was stirred in a hydrogen atmosphere (1 amt) at 25° for 25 min., then the catalyst was filtered off and sodium 2-ethylhexanoate (87 mg) was added. The organic solution was concentrated under reduced pressure and the sodium salt residue was diluted with water and purified by reverse phase chromatography. The aqueous solution was ice-dried to give the title compound as a white solid (90 mg).

IR(CDCl$_3$)V$_{max}$ cm$^{-1}$: 3375(O-H), 1749(C=O $\beta$ lactam), 1595(C=O & C=C);

$^1$H-MNR(300 MHz, CDCl$_3$): 4.77(m), 4.16–4.06(m), 4.08(dd), 3.31(dd), 3.11(s), 3.03(m), 1.89(m), 1.75(m), 1.6–1.2(m), 1.14(d).

EXAMPLE 44

Ethyl(4S,8S,9R,10S,12R)-4-methoxy-10-(1-(t-butydimethylsilyloxy)ethyl-11-oxo-1-azatricyclo[7.2.0.0$^{3,8}$]undec-2-ene-2-carboxylate To a solution of the intermediate 42 (0.7 g) in dry tetrahydrofuran (15 ml) under nitrogen at −10°, thionyl chloride (0.24 ml) and 2,6-lutidine(0.41 ml) were added. The reaction mixture was stirred at −10° for 30 min, then diluted with ethyl acetate (100 ml) and washed with saturated aq. ammonium chloride (2×80 ml) and brine (2×70 ml) dried and evaporated under vacuum. The oily residue (0.72 g) was dissolved in 1,4-dioxan (10 ml) and 2,6-lutidine (0.28 ml), sodium bromide (0.33 g) and triphenylphosphine (0.85 g) were added. The reaction mixture was stirred at 22° for 24 hrs, then diluted with ethyl acetate (50 ml) and washed with saturated aq. ammonium chloride (2×50 ml) and brine (2×50 ml), dried and concentrated under vacuum. The oily residue was chromatographed on silica gel, using cyclohexane/ethyl acetate 8/2 as eluant, to afford a colourless oil (0.66 g)(t.l.c. cyclohexane3ethyl acetate 1/1; Rf=0.3).

A solution of the crude oil (0.66 g), in 1,4-dioxan (10 ml) was heated at reflux for 4 hrs, diluted with ethyl acetate (30 ml) and washed with brine (2×50 ml), dried and concentrated under vacuum. The oily residue was chromatographed on silica gel, using cyclohexane/ethyl acetate 9/1 as eluant, to afford a colourless oil (0.13 g; t.l.c. cyclohexane/ethyl acetate 1/1 Rf=0.66).

IR(CDCl$_3$)V$_{max}$cm$^{-1}$: 1774(C=O $\beta$lactam), 1715(C=O ester), 1632(C=C);

EXAMPLE 45

Ethyl(4S,8S,(R,10S,12R)-4-methoxy-10-(1-hydroxyethyl)-11-oxo-1-azatricyclo[7.2.0.0$^{3,8}$]undec-2-ene-2-carboxylate To a solution of Example 45 (0.1 g) in tetrahydrofuran (4 ml), acetic acid (0.1 ml) and a 1.1M solution of N,N,N,N-tetrabutylammonium fluoride trihydrate (0.22 g) were added. The reaction mixture was stirred at 22° for 17 hrs, then diluted with diethyl ether (20 ml) and washed with 5% aq. sodium hydrogen carbonate (30 ml) and brine (30 ml), dried and concentrated under vacuum. The residue was chromatographed on silica gel, using diethyl ether/petroluem ether 1/1 as elutant to give the title compound as a colourless oil (40 mg; t.l.c. diethylether; Rf=0.32).

IR(CDCl$_3$)V$_{max}$cm$^{-1}$: 3607(O—H), 1772(C=) $\beta$ lactam), 1715(C=O ester), 1632(C=C);

$^1$H-MNR(300 MHz,CDCl$_3$): 4.96(t), 4.46–4.22(m), 4.19(dd), 3.23(s), 3.35–3.17(m), 3.24(dd), 2.08(m), 1.92–1.2(m), 1.36(d), 1.33(t).

Pharmacy Example

Dry Powder for Injection

| | Per Vial |
|---|---|
| Sodium(4S,8S,9R,10S,12R)-4-methoxy-10-(1-hydroxyethyl)-11-oxo-1-azatricyclo[7.2.0.0$^{3,8}$]undec-2-ene-2-carboxylate | 538 mg |

Fill sterile vials with the sterile sodium salt. Purge the vial head space with sterile nitrogen; close the vials using rubber plugs and metal overseals (applied by crimping). The product may be constituted by dissolving in Water for Injection (10 ml) or other suitable sterile vehicle for injection shortly before administration.

We claim:

1. A compound of formula (I)

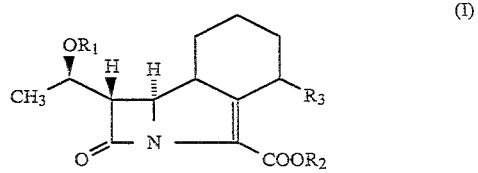

in which:

R$_1$ represents a hydrogen atom or a hydroxyl protecting group;

R$_2$ represents a hydrogen atom or a carboxyl protecting group; and

R$_3$ represents a hydrogen atom, a hydroxyl group, a hydroxymethyl group, a C$_{1-3}$alkyl group or a group XR$_4$ in which X represents an oxygen atom or the group S(O)n in which n is zero or the integer 1 or 2 and R$_4$ represents a C$_{1-5}$alkyl, C$_{3-7}$cycloalkyl or phenyl group, or when X is an oxygen or sulphur atom then R$_4$ may also represent the group AlkNR$_5$R$_6$ in which Alk represents a C$_{2-6}$ straight or branched alkylene chain, and R$_5$ and R$_6$ each independently represent a hydrogen atom or a C$_{1-4}$ alkyl group or R₅ represents a formyl, acetyl or iminomethyl group and R₆ represents a hydrogen atom or R₅ and R₆ together with the nitrogen atom to which they are attached form a pyrrolidino or piperidino ring, or R₃ represents a group (CH₂)ₘNR₇R₈ in which m is zero or one and R₇ and R₈ independently each represent a hydrogen atom or a C₁₋₄ alkyl group or R₇ represents a formyl, acetyl or iminomethyl group and R₈ represents a hydrogen atom, or R₃ and the carbon atom to which it is attached represent a keto group or a ketal derivative thereof;

or salts (including internal salts where appropriate), metabolically labile esters or solvates thereof.

2. A compound as claimed in claim 1 wherein R₁ and R₂ represent hydrogen atoms or physiologically acceptable salts (including internal salts), metabolically labile esters or solvates thereof.

3. A compound as claimed in claim 2 wherein R₃ represents an amino, aminomethyl, methylamino, hydroxy, hydroxymethyl, methyl, methoxy, ethoxy, isopropoxy, cyclopentoxy, aminoethoxy, methylthio, phenylthio or methylsulphinyl group or together with the carbon atom to which it is attached form a keto or dimethylketal group.

4. A compound as claimed in claim 1 of formula (Ie)

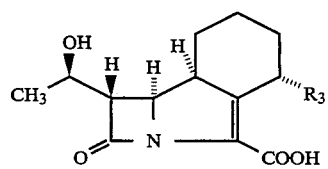

(Ie)

wherein R₃ represents an amino, aminomethyl, methylamino, hydroxy, hydroxymethyl, methoxy, ethoxy, isopropoxy, aminoethoxy, methylthio, methoxylsulphinyl or phenylthio group, or physiologically acceptable salts, metabolically labile esters or solvates thereof.

5. (4S,8S,9R,10S,12R)-4-methoxy-10-(1-hydroxyethyl)-11-oxo-1-azatricyclo[7.2.0.0³,⁸]undec-2-ene-2-carboxylic acid, or physiologically acceptable salts, metabolically labile esters or solvates thereof.

6. The compounds:
(4S,8S,9R,10S,12R)-4-methylthio-10-(1-hydroxyethyl)-11-oxo-1-azatricyclo[7.2.0.0³,⁸]undec-2-ene-2-carboxylic acid,
(4S,8S,9R,10S,12R)-4-methylsulphinyl-10-(1-hydroxyethyl)-11-oxo-1-azatricyclo[7.2.0.0³,⁸]undec-2-ene-2-carboxylic acid, and
(4S,8S,9R,10S,12R)-4-amino-10-(1-hydroxyethyl)-11-oxo-1-azatricyclo[7.2.0.0³,⁸]undec-2-ene-2-carboxylic acid, or physiologically acceptable salts, metabolically labile esters or solvates thereof.

7. A pharmaceutical composition for the treatment of bacterial infections in human or non-human animal bodies comprising an effective amount of a compound as claimed in claim 2 in admixture with one or more physiologically acceptable carriers or excipients.

8. A pharmaceutical composition for the treatment of bacterial infections in human or non-human animal bodies comprising an effective amount of a compound as claimed in claim 4 in admixture with one or more physiologically acceptable carriers or excipients.

9. A pharmaceutical composition for the treatment of bacterial infections in human or non-human animal bodies comprising an effective amount of a compound as claimed in claim 5 in admixture with one or more physiologically acceptable carriers or excipients.

10. A pharmaceutical composition for the treatment of bacterial infections in human or non-human animal bodies comprising an effective amount of a compound as claimed in claim 6 in admixture with one or more physiologically acceptable carriers or excipients.

11. A method of treatment of a human or non-human body to combat bacterial infections comprising administration to said body of an effective amount of a compound as claimed in claim 2.

12. A method of treatment of a human or non-human body to combat bacterial infections comprising administration to said body of an effective amount of a compound as claimed in claim 4.

13. A method of treatment of a human or non-human body to combat bacterial infections comprising administration to said body of an effective amount of a compound as claimed in claim 5.

14. A method of treatment of a human or non-human body to combat bacterial infections comprising administration to said body of an effective amount of a compound as claimed in claim 6.

15. A composition as claimed in claim 7 for topical administration to the human or non-human body.

16. A composition as claimed in claim 15 wherein the effective amount of the compound is 0.01–10%.

17. A composition as claimed in claim 16 wherein the effective amount of the compound is 0.01–1%.

18. A method as claimed in claim 11 wherein the compound is administered systemically.

19. A method as claimed in claim 18 wherein the effective amount of the compound is 5–100 mg/kg body weight.

20. A method as claimed in claim 19 wherein the effective amount of the compound is 10–60 mg/kg body weight.

21. Sodium (4S,8S,9R,10S,12R)-4-methoxy-10-(1-hydroxyethyl)-11-oxo-1-azatricyclo[7.2.0.0.³,⁸]undec-2-ene-2-carboxylate.

22. A pharmaceutical composition for the treatment of bacterial infections in human or non-human animal bodies comprising an effective amount of a compound as claimed in claim 21 in admixture with one or more physiologically acceptable carriers or excipients.

23. A method of treatment of a human or non-human animal body to combat bacterial infections comprising administration to said body of an effective amount of a compound as claimed in claim 21.

* * * * *